United States Patent [19]

Hess et al.

[11] 4,036,832

[45] July 19, 1977

[54] 15-SUBSTITUTED-ω-PENTANORPROSTA-GLANDINS

[75] Inventors: Hans-Jurgen E. Hess, Old Lyme; Michael R. Johnson, Gales Ferry; Jasjit S. Bindra, Groton; Thomas K. Schaaf, Old Lyme, all of Conn.

[73] Assignee: Pfizer Inc., N.Y.

[21] Appl. No.: 705,767

[22] Filed: July 15, 1976

Related U.S. Application Data

[60] Division of Ser. No. 485,599, July 3, 1974, Pat. No. 3,971,826, which is a continuation-in-part of Ser. No. 425,519, Dec. 17, 1973, abandoned, which is a continuation-in-part of Ser. No. 271,220, July 13, 1972, abandoned.

[51] Int. Cl.$^2$ .................. C07D 407/02; C07D 309/02

[52] U.S. Cl. ........................... 260/240 R; 260/240.1; 260/340.5; 260/343.6; 260/345.7; 260/468 D; 260/514 D; 260/520 B; 260/967; 424/308

[58] Field of Search ............ 260/240 R, 240.1, 345.7, 260/340.5

[56] References Cited

U.S. PATENT DOCUMENTS

| 3,671,570 | 6/1972 | Bagli et al. | 260/468 D |
|---|---|---|---|
| 3,931,289 | 1/1976 | Bundy | 260/468 D |

Primary Examiner—Arthur P. Demers
Attorney, Agent, or Firm—Connolly and Hutz

[57] ABSTRACT

The 15-substituted-ω-pentanorprostaglandins and various intermediates employed in their preparation. The novel prostaglandins of this invention have been found to have activity profiles comparable to the parent prostaglandins, but exhibit a greater tissue specificity of action.

4 Claims, No Drawings

15-SUBSTITUTED-ω-PENTANORPROSTAGLANDINS

CROSS REFERENCE TO RELATED APPLICATIONS

This application is a division of application Ser. No. 485,599 filed July 3, 1974 now U.S. Pat. No. 3,971,826, which, in turn, is a continuation-in-part of application Ser. No. 425,519 filed Dec. 17, 1973 and now abandoned, which, in turn, is a continuation-in-part of application Ser. No. 271,220 filed July 13, 1972 and now abandoned.

BACKGROUND OF THE INVENTION

This invention relates to certain novel analogs of the naturally occurring prostaglandins. In particular, it relates to novel 15-substituted-ω-pentanorprostaglandins and various novel intermediates useful in their preparation.

The prostaglandins are C-20 unsaturated fatty acids which exhibit diverse physiological effects. For instance, the prostaglandins of the E and A series are potent vasodilators (Bergstrom, et al., *Acta Physiol. Scand.* 64:332-33 1965 and Bergstrom, et al., *Life Sci.* 6:449-455, 1967) and lower systemic arterial blood pressure (vasodepression) on intravenous administration (Weeks and King, *Federation Proc.* 23:327, 1964; Bergstrom, et al., 1965, op. cit.; Carlson, et al., *Acta Med. Scand.* 183:423-430, 1968; and Carlson, et al., *Acta Physiol. Scand.* 75:161-169, 1969). Another well known physiological action for $PGE_1$ and $PGE_2$ is as a bronochodilator (Cuthbert, Brit. Med. j. 4:723-726, 1969).

Still another important physiological role for the natural prostaglandins is in connection with the reproductive cycle. $PGE_2$ is known to possess the ability to induce labor (Karim, et al., *J. Obstet. Gynaec. Brit. Cwlth.* 77:200-210, 1970), to induce therapeutic abortion (Bygdeman, et al., *Contraception*, 4, 293 (1971) and to be useful for control of fertility (Karim, *Contraception*, 3, 173 (1971)). Patents have been obtained for several prostaglandins of the E and F series as inducers of labor in mammals (Belgian Pat. No. 754,158 and West German Pat. No. 2,034,641), and on $PGF_1$, $F_2$, and $F_3$ for control of the reproductive cycle (South African Patent 69/6089). It has been shown that luteolysis can take place as a result of administration of $PGF_2\alpha$[Labhsetwar, Nature 230 528 (1971)] and hence prostagalandins have utility for fertility control by a process in which smooth muscle stimulation is not necessary.

Still another known physiological activities for $PGE_1$ are in the inhibition of gastric acid secretion (Shaw and Ramwell, In: *Worcester Symp. on Prostaglandins*, New York, Wiley, 1968, p. 55-64) and also of platelet aggregation (Emmons, et al., Brit. Med. J. 2:468-472, 1967).

It is now known that such physiological effects will be produced in vivo for only a short period, following the administration of a prostaglandin. A substantial body of evidence indicates that the reason for this rapid cessation of activity is that the natural prostaglandins are quickly and efficiently metabolically deactivated by β-oxidation of the carboxylic acid side-chain and by oxidation of the 15α-hydroxyl group (Anggard, et al., *Acta. Physiol. Scand.*, 81, 396 (1971) and references cited therein). It has been shown that placing a 15-alkyl group in the prostaglandins has the effect of increasing the duration of action possibly by preventing the oxidation of the C15-hydroxyl [Yankee and Bundy, JACS 94, 3651 (1972)], Kirton and Forbes, *Prostaglandins*, 1, 319 (1972).

It was, of course, considered desirable to create analogs of the prostaglandins which would have physiological activities equivalent to the natural compounds, but in which the selectivity of action and the duration of the activity would be increased. Increased selectivity of action would be expected to alleviate the severe side effects, particularly gastrointestinal side effects, frequently observed following systemic administration of the natural prostaglandins (Lancet, 536, 1971).

SUMMARY OF THE INVENTION

These needs are met by the novel compounds of this invention, the 15-substituted-ω-pentanorprostaglandins, having the structure:

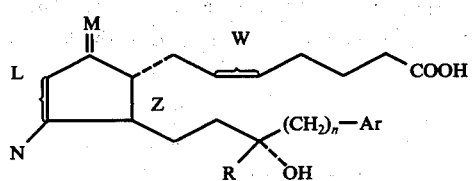

and their $C_{15}$ epimers, wherein Ar is α- or β-naphthyl; 3,4-methylenedioxyphenyl; or monosubstituted phenyl wherein said substitutent is phenyl;

R is hydrogen or lower alkyl;

n is an interger from 1 to 5;

W and L are each a single bond or cis double bond; Z is a single bond or trans double bond; with the proviso that when n is one and Z is a single bond, W is a single bond;

M is keto,

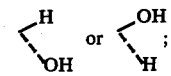

N is hydrogen or α-hydroxyl;

and wherein L, M and N are so selected as to complete the structure of a prostaglandin of the A, E or F series.

A preferred group of compounds of this invention have the formula:

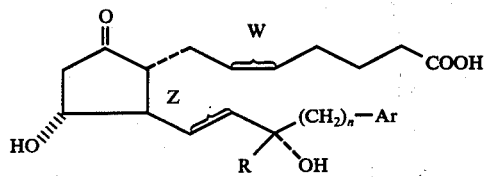

other preferred compounds of the present invention have the formula:

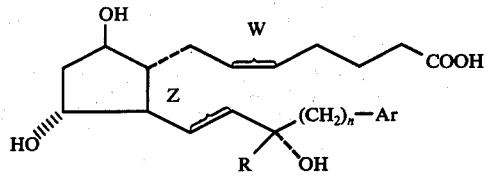

and still other preferred compounds of the present invention are those of the formula:

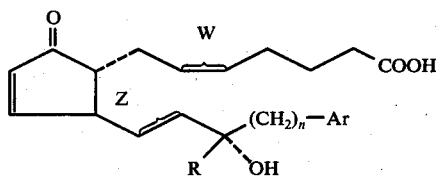

wherein W, Z, Ar, n and R are as defined above.

In addition to said 15-substituted-ω-pentanorprostaglandins wherein the prostaglandin is $PGF_{1\alpha}$, $PGE_1$, $PGA_1$: 13,14-dihydro $PGF_1\alpha$, $PGE_1$, and $PGA_1$; $PGF_2\alpha$, $PGE_2$, $PGA_2$; and when n is from 2-5, the 13,14-dihydro $PGF_2\alpha$, $PGE_2$, and $PGA_2$; and 15-lower alkyl derivatives of the above compounds, this invention further comprises a compound of the structure:

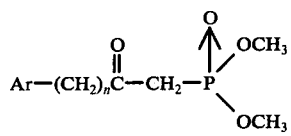

wherein Ar is α or β-naphthyl; phenyl; 3,4-dimethoxyphenyl; 3,4-methylenedioxyphenyl; 3,4,5-trimethoxyphenyl or monosubstituted phenyl wherein said substitutent is halo, trifluoromethyl, phenyl, lower alkyl or lower alkoxy; and n is an interger from 1 to 5, a useful reagent for preparation of the novel prostaglandins; and useful intermediates for these prostaglandins as follows: a compound of the structure

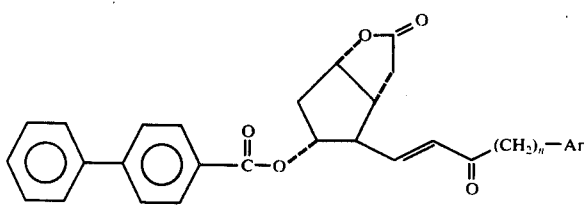

a compound of the structure:

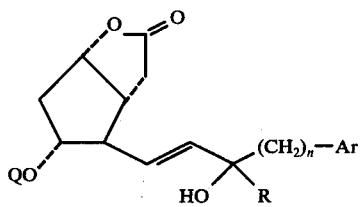

wherein R is hydrogen or lower alkyl; and Q is hydrogen or parabiphenylcarbonyl;

a compound of the structure:

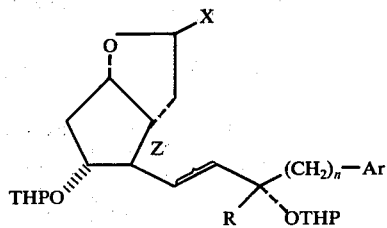

wherein THP is tetrahydropyranyl, n is an integer from 1 to 5; z is a single bond or a trans double bond with the proviso that when n is 1, z is a trans double bond; and X is

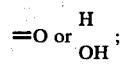

a compound of the structure:

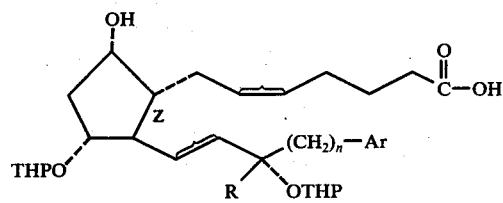

wherein w is a single bond or a cis double bond and z is a single bond or a trans double bond; with the proviso that when n is 1, Z is a trans double bond;

a compound of the structure:

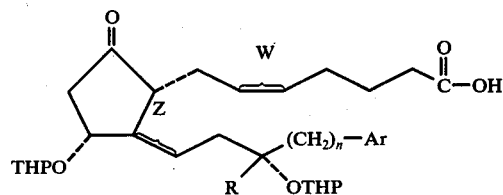

wherein w, z, THP, R, Ar and n are as previously defined, a compound of the structure:

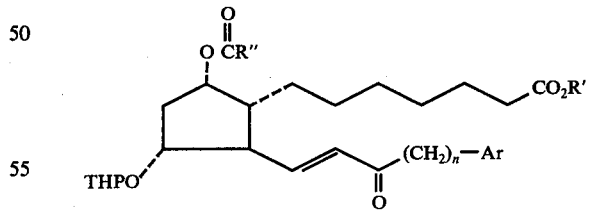

wherein R' is lower alkyl;

R" is lower alkyl, aralkyl of from 7 to 10 carbom atoms, phenyl and substituted phenyl wherein said substituent is lower alkyl, lower alkoxy, halo, trifluorormethyl or phenyl; and THP, n, and Ar are as previously defined; and especially 16-p-biphenyl-ω-tetranor $PGE_2$, 16-β-naphthyl-ω-tetranor $PGE_2$, 16-β-naphthyl-ω-tetranor $PGE_0$, 16β-naphthyl-ω-tetranor-$PGF_2\beta$, and 16-p-biphenyl-ω-tetranor $PGE_1$.

It will be understood by those skilled in the art that in structures depicting hemiacetals, no sterochemistry is implied at the lactol carbon.

It will be further understood that as herein used, the expression "prostaglandin of the 'zero' series," for example PGE$_0$, refers to prostaglandin in which the 5-6 and 13-14 double bonds have been saturated; i.e.: PGE$_0$ is 5-6, 13-14, tetrahydro PGE$_2$. In addition, the phrases "zero series", "one series" or "two series" as herein employed refer to the degree of unsaturation in the side chains, e.g., PGE$_2$, PGA$_2$ and PGF$_2\alpha$, are prostaglandins of the "two series" whereas PGE$_1$, PGF$_1\alpha$ and PGA$_1$ are prostaglandins of the "one series". Furthermore as herein employed the phrase lower "alkyl group" refers to alkyl groups containing from 1 to 4 carbon atoms.

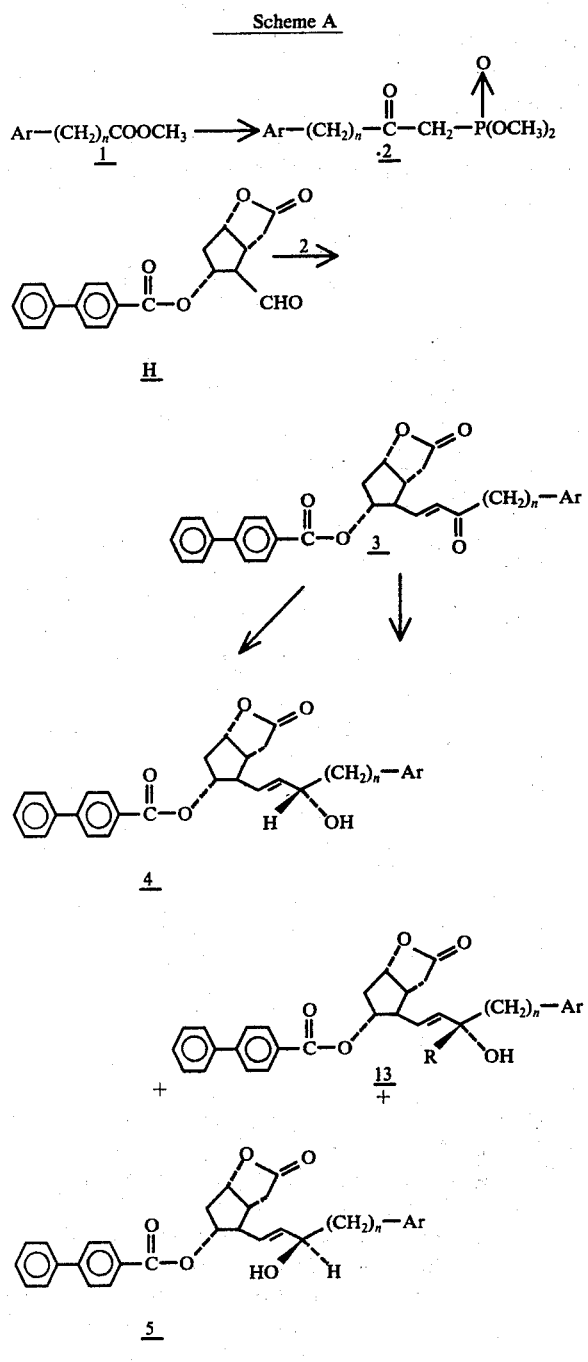

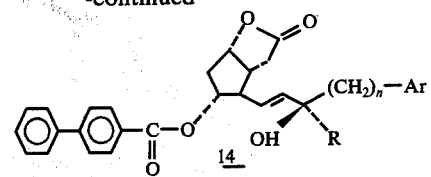

DETAILED DESCRIPTION OF THE INVENTION

As shown in scheme A, the first step (1 → 2) is the condensation of the appropriate ester with a dialkyl methylphosphonate to produce ketophosphonate 2. Typically, the desired methyl ester is condensed with dimethyl methyl phosphonate.

In 2 → 3 the ketophosphonate 2 is caused to react with the known ]Corey et al., J. Am. Chem. Soc. 93, 1491 (1971)]alkehyde H to produce, after chromatography or crystallization, the enone 3.

The enone 3 can be converted to a mixture of tertiary alcohols 13 and 14 by reaction with the appropriate lithium alkyl and the isomeric 13 and 14 can be separated by column, thin layer, or high pressure chromatography. The enone 3 can be reduced with zinc borohydride or lithium triethyl borohydride to a mixture of alcohols, 4 and 5 which can be separated as above. In this reaction ethers such as tetrahydrofuran or 1,2 dimethoxy ethane are usually employed as solvents. Further transformations of 4 are shown on scheme B:

4 → 6 is a base catalized transesterification in which the p-biphenyl-carbonyl protecting group is removed. This is most conveniently conducted with potassium carbonate in methanol or methanol-tetrahydrofuran solvent. 6 → 7 involves the protection of the two free hydroxyl groups with an acid-labile protecting group. Any sufficiently acid-labile group is satisfactory; however, the most usual one is tetrahydropyranyl, which can be incorporated in the molecule by treatment with dihydropyran and an acid catalyst in an anhydrous medium. The catalyst is usually p-toluenesulfonic acid.

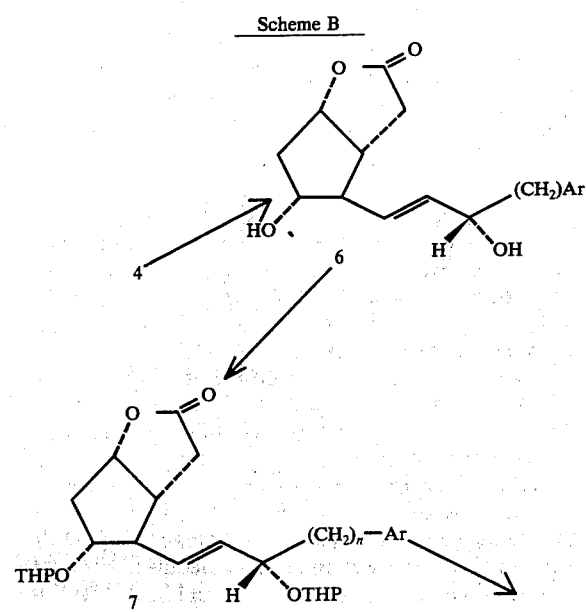

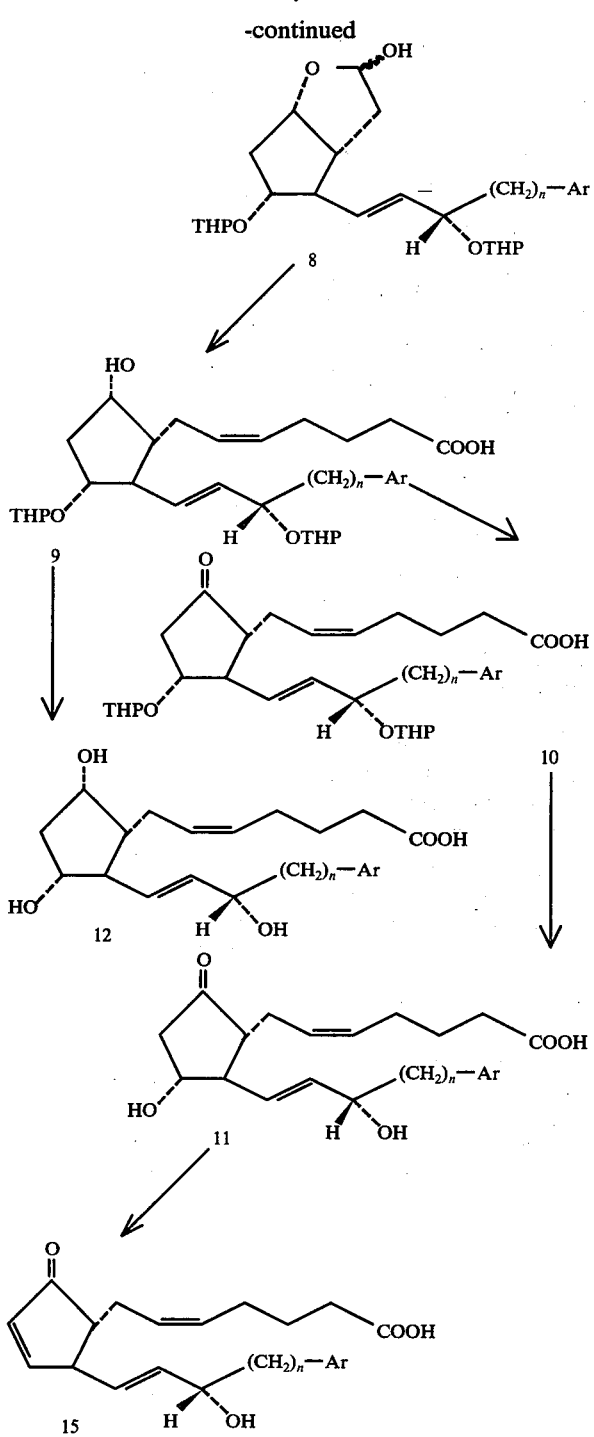

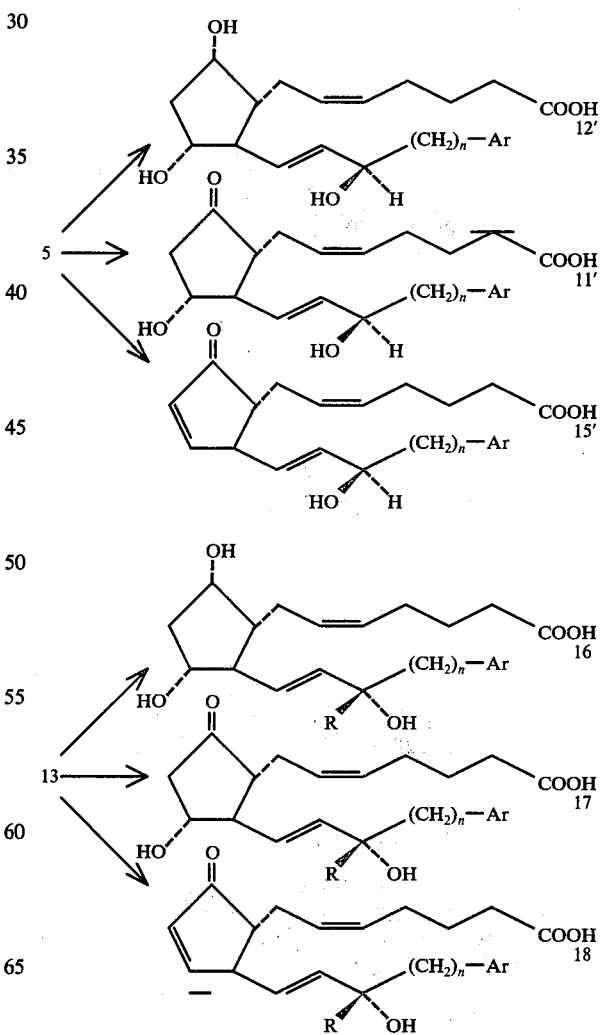

accomplished most often by use of 65% aqueous acetic acid. The product is purified as above.

9 → 10 is an oxidation of the secondary alcohol 9 to the ketone 10. This may be accomplished using any oxidizing agent which does not attack double bonds; however, the Jones reagent is usually preferred. The product is purified as above.

10 → 11 is carried out in the same manner as 9 → 12. The product is purified as above. Reduction of compound 11 with sodium borohydride will provide the 9β isomer of prostaglandin analogs of the F series, i.e. $PGF_{2\beta}$ compounds. These may also be obtained via sodium borohydride reduction of 10 followed by hydrolysis as described above for 10–11.

11 → 15 is an acid-catalyzed dehydration. Any acid may be used for the process which does not cause extensive decomposition of the product, but the most usual procedure consists of dissolving 11 in an excess of 97% formic acid 11 in an excess of 97% formic acid followed 13 by dilution with ice water and extraction of the product after the starting material has been consumed.

7 → 8 is a reduction of the lactone 7 to the hemiacetal 8 using diisobutyl aluminum hydride in an inert solvent. Low reaction temperatures are preferred and −60° to −70° C. are usual. However, higher temperature may be employed if over-reduction does not occur. 8 is purified, if desired, by column chromatography.

8 → 9 is a Wittig condensation in which hemiacetal 8 is reacted with (4-carbohydroxy-n-butyl)triphenylphosphonium bromide in dimethyl sulfoxide, in the presence of sodium methylsulfinyl methide. 9 is purified as above.

The conversion 9 → 12 is an acidic hydrolysis of the tetrahydropyranyl groups. Any acid may be used which does not cause destruction of the molecule in the course of the removal of the protecting groupl however, this is -continued

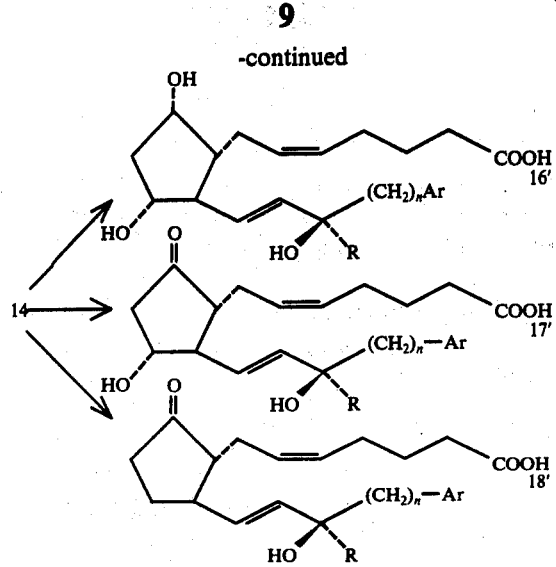

The product is purified as above.

As is illustrated in scheme C, 5, 13 and 14 may be substituted for 4 in scheme B to provide prostaglandin derivatives 12'–18'.

Scheme D illustrates the synthesis of precursors to the 13,14-dihydro-15-substituted-ω-pentanorprostaglandins.

In 3 → 19 + 19' the enone 3 is reduced to the tetrahydro compound through the use of any of the complex metal hydride reducing agents, LiAlH$_4$, NaBH$_4$, KBH$_4$, LiBH$_4$ and Zn(BH$_4$)$_2$. Especially preferred is NaBH$_4$. The products, 19 and 19', are separated from each other by column chromatography.

Furthermore, the compounds 4 and 5 of Scheme A can be reduced catalytically with hydrogen to 19 and 19' respectively. The stage at which the double bond is reduced is not critical, and hydrogenation of 6 or 7 of scheme B will also afford useful intermediates for the 13,14 dihydro prostaglandin analogs of the present invention. This reduction may be achieved with either a homogenous catalyst such as tristriphenylphosphinerhodiumchloride, or with a heterogeneous catalyst such as platinum, palladium or rhodium. In a similar way the precursors to the 15-lower alkyl-15-substituted-ω-pentanorprostaglandins are synthesized by substituting compound 13 and 14 for 4 and 5 respectively, in the synthesis just described.

The conversion of 19, 19', 20' and 20 to their respective prostaglandins follows the route shown in scheme B when 4 is replaced by 19, 19', 20' and 20 to yield the 13,14-dihydro PGE$_2$, PGA$_2$ and PGF$_2$ series of prostaglandin derivatives containing hydrogen or lower alkyl group at carbon 15.

Scheme E illustrates the preparation of the various reduced 15-substituted-ω-pentanorprostaglandin precursors:

19 → 22 is carried out as illustrated on Scheme B for 4 → 9. 22 can be used as both a precursor to a 13,14-dihydro 15-substituted-ω-pentanorprostaglandin of the 2-series or as an intermediate to 23, a precursor to a 13,14-dihydro-15-substituted-ω-pentanorprostaglandin of the 1-series. 22 → 23 is carried out by catalytic hydrogenation using the catalyst described for the reduction of 4 → 19 of Scheme D. Intermediates of the type 21 are prepared by selective reduction of the 5–6 cis double bond at low temperature using catalysts such as those described for 4 → 19 and 17 → 23. Especially preferred for this reduction is the use of palladium on carbon as a catalyst and a reaction temperature of −20°. Intermediates of the type 21 are not only precursors to 15-substituted-ω-pentanorprostaglandins of the 1-series through the route 9 → 15 of scheme B, but also as a precursor to compounds of the type 23 through the route already discussed for 22 → 23.

Scheme D

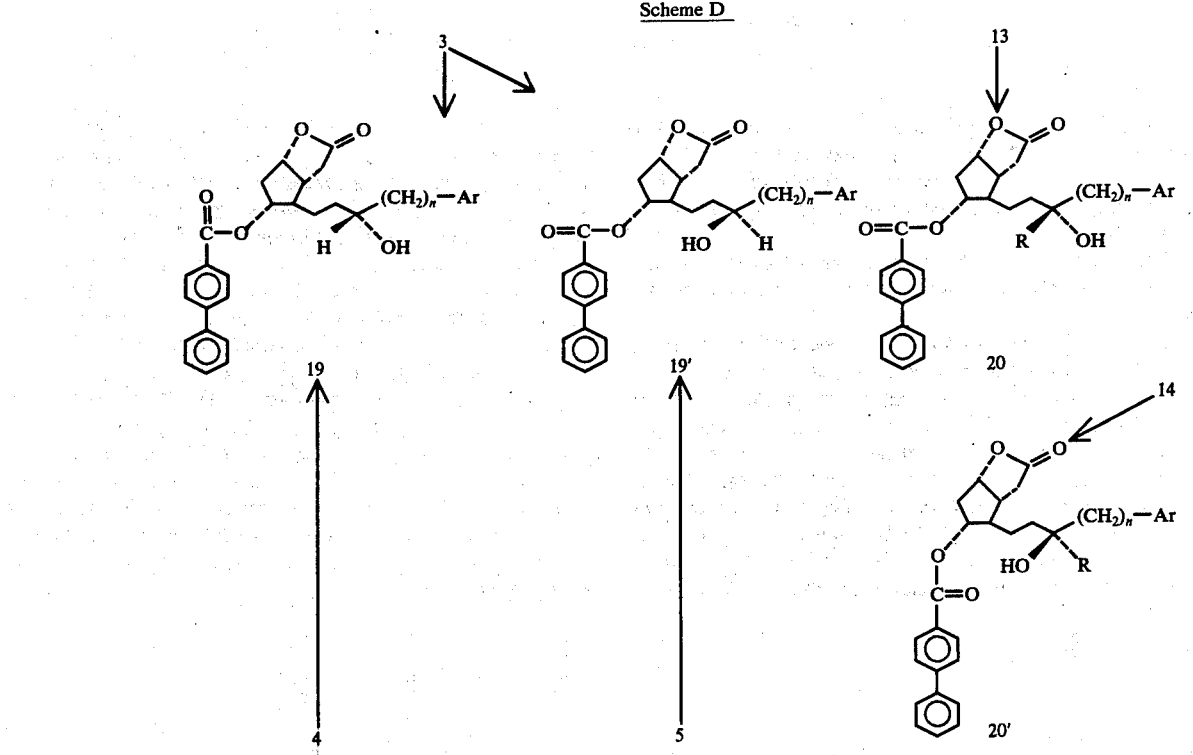

Scheme E

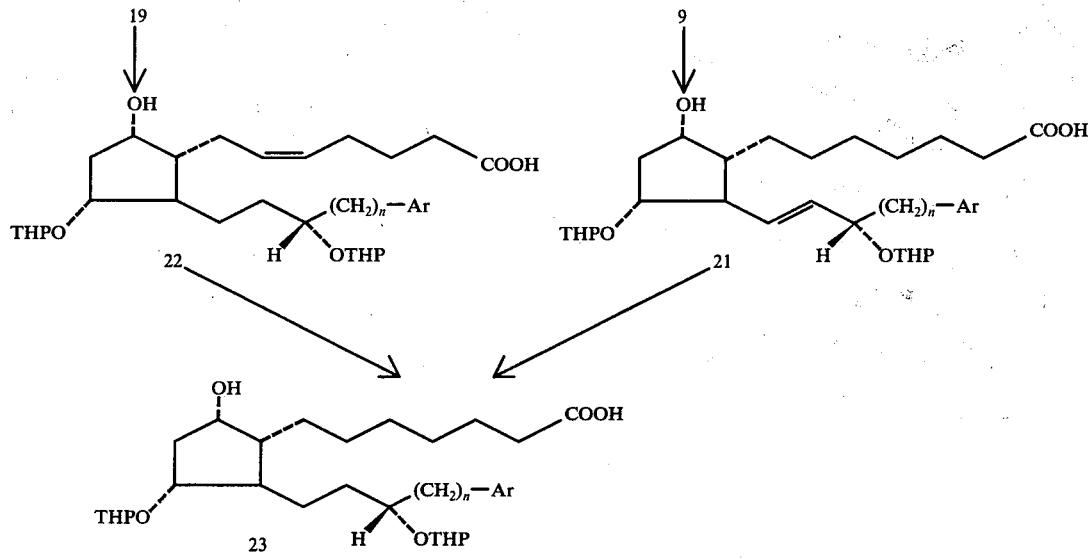

Furthermore, the 15-substituted-ω-pentanorprostaglandins by 19, 19', 20' and 20 to yield the 13,14-dihydro PGE$_2$, PGA$_2$ and PGF$_2$ series of prostaglandin derivatives containing hydrogen or lower alkyl group at carbon 15.

Scheme E illustrates the preparation of the various reduced 15-substituted-ω-pentanorprostaglandin precursors:

19 → 22 is carried out as illustrated on Scheme B for 4 → 9. 22 can be used as both a precursor to a 13,14-dihydro 15-substituted-ω-pentanorprostaglandin of the 2-series or as an intermediate to 23, a precursor to a 13,14-dihydro-15-substituted-ω-pentanorprostaglandin of the 1-series. 22 → 23 is carried out by catalytic hydrogenation using the catalyst described for the reduction of 4 → 19 of Scheme D. Intermediates of the type 21 are prepared by selective reduction of the 5-6 cis double bond at low temperature using catalysts such as those described for 4 → 19 and 17 → 23. Especially preferred for this reduction is the use of palladium on carbon as a catalyst and a reaction temperature of —20°. Intermediates of the type 21 are not only precursors to 15-substituted-ω-pentanorprostaglandins of the 1-series through the route 9 → 15 of scheme B, but also as a precursor to compounds of the type 23 through the route already discussed for 22 → 23. Furthermore, the 15-substituted-ω-pentanorprostaglandins of the E$_1$ and F$_1$α series may be obtained directly from the corresponding prostaglandin analog of the 2-series by first protecting the hydroxyl by introducing dimethyl isopropyl silyl groups, of the E$_1$ and F$_1$α series may be obtained directly from the corresponding prostaglandin analog of the 2-series by first protecting the hydroxyl by introducing dimethyl isopropyl silyl groups, reducing selectively the cis double bond, and removing the protecting group.

Scheme F

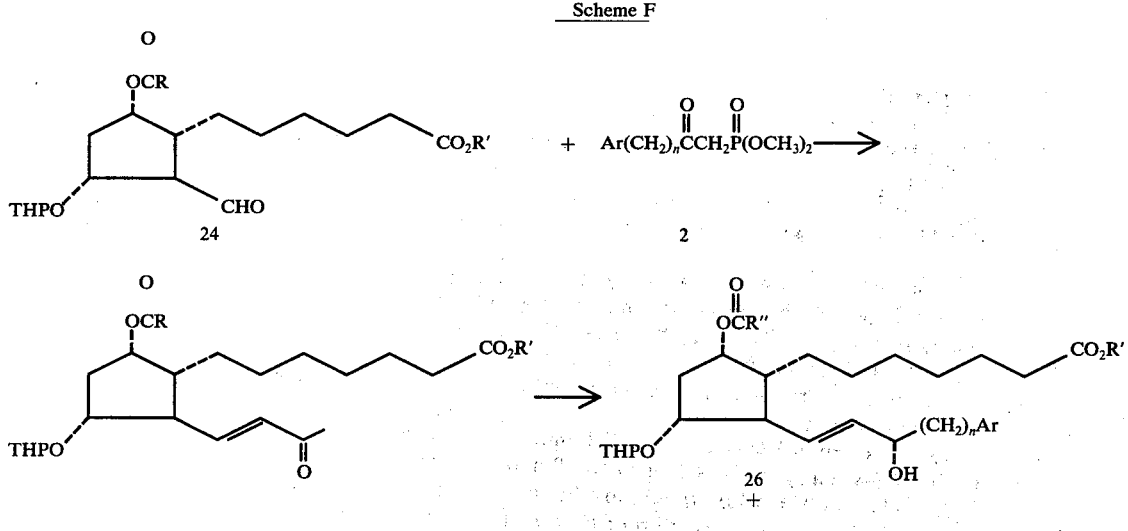

-continued
Scheme F

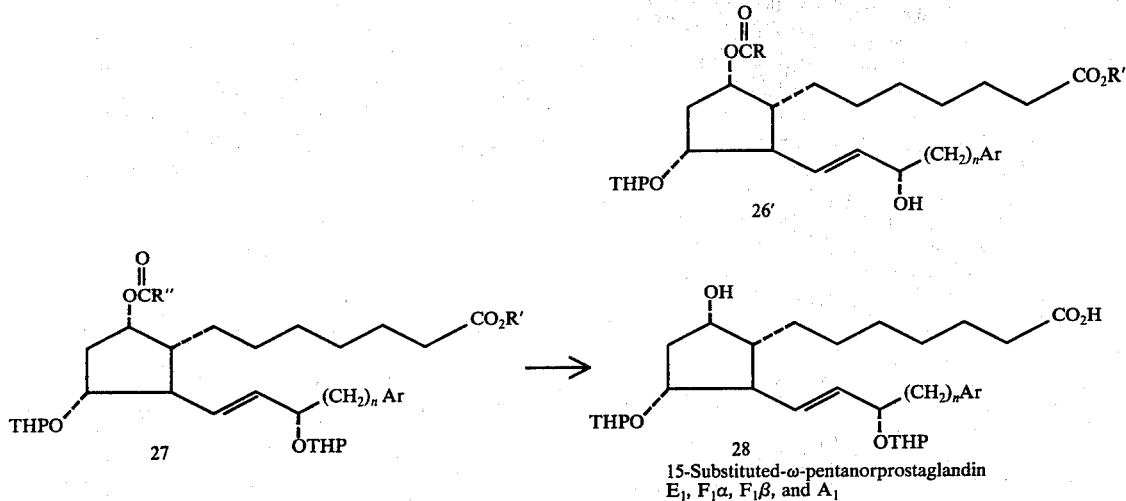

15-Substituted-ω-pentanorprostaglandin
$E_1$, $F_1\alpha$, $F_1\beta$, and $A_1$ Alternatively, 15-substituted-ω-pentanorprostaglandins of the 1-series may be prepared as outlined in scheme F.

In 24 → 25 the ketophosphonate 2 is caused to react with the aldehyde 24 to produce, after purification, the enone 25.

The enone 25 can be reduced with zinc borohydride or lithium triethylborohydride to a mixture of alcohols 26 and 26' which may be separated by column, thin layer, or high pressure chromatography. 26 → 27 involves the protection of the free hydroxyl group with an acid-labile protecting group. Any sufficiently acid-labile group is satisfactory; however, the most usual one is tetrahydropyranyl, which can be incorporated in the molecule by treatment with dihydropyran and an acid catalyst such as p-toluenesulfonic acid in an anhydrous medium.

27 → 28 involves cleavage of the ester functions with aqueous hydroxide; an inert co-soluent may be desired to facilitate solution of 27. The intermediate 28 may be converted into the 15-substituted-ω-pentanorprostaglandin $E_1$, $F_1\alpha$, $F_1\beta$, and $A_1$ as described above.

The introduction of the protecting group is usually accomplished by treatment of the prostaglandin analog with dimethyl isopropyl chlorosilane and triethylamine, the reduction is accomplished as discussed above for 9 → 21 and removal of the protecting group is accomplished by contacting the reduced protected compound with 3:1 acetic acid:water for 10 minutes or until reaction is substantially complete.

The $C_{15}$ epimers of 21, 22 and 23 can be used as precursors to the 15-epi series of prostaglandin derivatives described above, and 15-lower-alkyl-15-substituted-ω-pentanorprostaglandins reduced at the 5-6 and/or the 13,14 position and their $C_{15}$ epimers can be prepared from the appropriately substituted analogs of 9 and 19 whose syntheses follow those of Scheme A and B.

13,14-dihydro-15-lower alkyl-15-substituted-ω-pentanorprostaglandins are available from the appropriately substituted precursors via Scheme E.

In the foregoing procedures, where purification by chromatography is desired, appropriate chromatographic supports include neutral alumina and silica gel and 6200 mesh silica gel is generally preferred. The chromatography is suitably conducted in reaction-inert solvents such as ether, ethyl acetate, benzene, chloroform, methylene chloride, cyclohexane and n-hexane, as further illustrated in the appended examplex.

In numerous in vivo and in vitro tests we have demonstrated that the new prostaglandin analogs possess physiological activities comparable to those exhibited by the natural prostaglandins (see above). These tests include, among others, a test for effect on isolated smooth muscle from guinea pig uterus, guinea pig ileum and rat uterus, inhibition of norepinephrine-induced lipolysis in isolated rat fat cells, inhibition of histamine-induced bronchospasm in the guinea pig effect, on dog blood pressure, inhibition of stress- induced ulceration in the rat, inhibition of ADP- or collagen-induced aggregation of blood platelets effect on pentagastrin induced acid secretion in the rat, and effect on diarrhea in mice.

The physiological responses observed in these tests are useful in determining the utility of the test substance for the treatment of various natural and pathological conditions. Such determined utilities include: antihypertensive activity, bronchodilator activity, antithrombogenic activity, antiulcer activity, smooth muscle activity [useful as an anti-fertility agent, for the induction of labor, and as an abortifacient], and anti-fertility activity through a mechanism not affecting smooth muscle, for example, luteolytic mechanisms.

The novel compounds of this invention possess highly selective activity profiles compared with the corresponding naturally occurring prostaglandins and, in many cases, exhibit a longer duration of action. A prime example of the therapeutic importance of these prostaglandin analogs is the efficacy of 16-(β-naphthyl)-ω-tetranorprostaglandin $E_2$ which exhibits hypotensive activity of greatly enhanced potency and duration as compared with $PGE_2$ itself. At the same time, the smooth muscle stimulating activity is markedly depressed in comparison with $PGE_2$.

In a similar manner, the other 16-Ar-substituted $PGE_o$ (tetrohydro $PGE_2$), $PGE_2$, and $PGE_{2\beta}$ analogs as well as the novel 15-substituted-ω-pentanorprostaglandins of the A series exhibit desirable hypotensive activity.

The 17, 18, 19, and 20-substituted prostaglandins of the E and F series of this invention exhibit outstanding smooth muscle stimulating or luteolytic activity useful for fertility control, abortion, and induction of labor in humans or the synchronization of the oestrus cycle in domestic animals, while at the same time having reduced blood pressure effects. The 16 substituted-ω-tetranorprostaglandins of the A series, via the 16 Ar, 17Ar, 18 Ar and 20 Ar-substituted prostaglandin analogs of the A series have useful blood pressure reducing properties as well as the ability to reduce gastric secretion thus making them useful in the treament of hypertension and peptic ulcers.

Furthermore, 16-p-biphenyl-ω-tetranorprostaglandin $E_2$ exhibits high bronchodilator activity with reduced non-vascular smooth muscle and hypotensive activity. In similar fashion, the 16-p-biphenyl substituted-ω-tetranorprostaglandin $E_1$ and $E_0$ analogs of the present invention display desirable bronchodilator activity.

The novel 15 lower alkyl compounds of this invention have the same profile of activity as the prostaglandin analogs of this invention, where R is hydrogen, from which they are derived. The prostaglandin analogs which have a beta hydroxyl at C15 and possess a C15 lower alkyl group have action which is similar to their epimers. In some cases, however, the selectivity that these compounds display exceeds that of the epimeric compounds.

The new compounds of this invention can be used in a variety of pharmaceutical preparations which contain the compound or a pharmaceutically acceptable salt thereof, and they may be administered in the same manner as natural prostaglandins by a variety of routes, such as intravenous, oral and topical, including aerosol, intravaginal, and intranasal, among others.

For induction of abortion an aqueous suspension of a 17-substituted-ω-trisnorprostaglandin of the E or F series or tablets would appropriately be administered at oral doses of about 1–20 mg., with 1–7 doses per day being employed. For intravaginal administration a suitable formulation would be lactose tablets or an impregnated tampon of the same agent. For such treatments suitable doses would be from about 1–20 mg/dose for the 17-Ar $PGE_2$ derivative or from about 10–200 mg/dose for the 17-Ar $PGF_2\alpha$ derivative, with 1 to 7 doses being employed.

Alternatively, for abortion, the 17-substituted-ω-trisnorprostaglandins can be administered intra-amniotically at doses of 5–40 mg., 1–5 times per day, or infused intravenously at doses of 5–500 μg/minute for a period of from about 1–24 hours.

Another suitable use for the 17, 18, 19 and 20-Ar-substituted prostaglandin analogs of the E and F series of this invention is as inducers of labor. For this purpose an ethanol-saline solution of a 17 substituted--trisnor $PGF_{2\alpha}$ or $PGE_2$ derivative can be employed as an intravaneous infusion in the amount of from about 0.05–50 μg/ minute for from about 1–10 hours.

For synchronization of oestrus in domestic farm animals, the 17-Ar substituted-ω-trisnorprostaglandin $F_2\alpha$ can be administered by IM injection at doses of 0.25 to 50 mg. with 1 to 4 doses being employed.

To produce bronchodilation or to increase nasal patency, an appropriate dosage form would be an aqueous ethanolic solution of 16-p-biphenyl-substituted-tetranor $PGE_1$ or $PGE_2$ employed as an aerosol using fluorinated hydrocarbons as propellant in the amount of from about 3–500 μg/dose.

15 substituted-ω-pentanorprostaglandins of the A series as well as 16-(β-naphthyl)-ω-tetranorprostaglandins of the $E_2$, $E_1$ and $E_0$ as well as the 16-(β-naphthyl) $F\beta$ series are useful hypotensive agents. For treatment of hypertension these drugs could appropriately be administered as an intravenous injection at doses of about 0.5–10 μg/kg or preferably in the form of capsules or tablets at doses of 0.005 to 0.5 mg/kg/day.

The 15-substituted-ω-pentanorprostaglandins of the A series are also useful for the treatment of peptic ulcers. For this purpose they may be administered in capsules or tablets at doses of from 0.005 to 0.5 mg/kg/day.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol, and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the scope of the appended claims. In these examples it will be appreciated that all temperatures are expressed in Centigrade, all melting and boiling points are uncorrected and all biological test data is expressed in terms of % activity of $PGE_2$ or administered at the same level (i.e., $PGE_2 = 100$) unless otherwise noted.

Each of the novel compounds of the present invention are also useful in the form of their para-phenylphenol esters. These specific esters are valuable because they are vary easily crystallized, thereby afferding the opportunity to recover them in highly pure form and outstanding yield whereas prostaglandins in general ordinarily present severe crystallization problems. The new para-phenylphenol esters exhibit the activities of the corresponding parent novel compounds and in addition posses the advantage of a flattened activity versus time curve which is often advantageous. The new compounds in the form of the para-phenylphenol esters are prepared by procedures already described with appropriate substitution of corresponding intermediates in paraphenylphenol ester form for the intermediates employed in the foregoing reaction schemes. Thus, for example, compounds 9 and 10 may be esterified with para-phenylphenol in the presence of dicyclohexylcarbodiimide to provide para-phenylphenol esters of precursors to 15 omega pentanorprostaglandin para-phenylphenol esters. These can, through steps 9–12, 10–11, and 11–12, be converted to the novel para-phenylphenol esters mentioned above. Further, compounds 11, 12 and 15 can likewise be esterified with para-phenylphenol and dicyclohexylcarbodiimide to provide the desired esters.

The biological data given below was obtained using the following procedures:

HISTAMINE-INDUCED BRONCHOCONSTRICTION —GUINEA PIGS.

Bronchodilator activities were evaluated in conscious female Reed-Willet guinea pigs (200 to 250 g) fasted overnight according to the method of Van Arman, Miller and O'Malley (1). At a pre-selected interval (pre-challenge interval) following oral or aerosol administration of water or the test drug in water, each animal was challanged with histamine aerosol as follows: a 0.4% aqueous solution of histamine was placed in a Vaponephrine Standard Nebulizer (Vaponephrine Company, Edision, New Jersey) and sprayed under an air pressure of 6 lb/in² into a closed 8 × 8 × 12 inch transparent plastic container for one min. Immediately thereafter, the guinea pig was placed in the container. The respiratory status (a reflection of bronchoconstriction) of the guinea pig after one min in the container was scored as follows: 0, normal breathing; 1, slightly deepened breathing; 2, labored breathing; 3, severely labored breathing and ataxia; 4, unconsciousness. The scores for a control group and a test group (8 animals/group) were summed and compared and the difference expressed as percent protection. (1)

1. VAN ARMAN, C.G., Miller, L.M. and O'Malley, M.P.: SC10,049: a catacholamine bronchodilator and hyperglycemic agent. J. Pharmacol. Exp. Ther. 133 90–97, 1961.

DOG BLOOD PRESSURE

Mondrel dogs were anesthetized with sodium pentobarbitol, 30 mg/kg/i.v. Femoral artery blood pressure was measured with a mercury manometer and recorded on smoked paper and heart rate was determined from electrocardiograms recorded from subcutaneous electrodes. Drugs were given through a cannula in a femoral vein.

ISOLATED GASTROINTESTINAL AND REPRODUCTIVE TISSUE

All measurements were made in a 2 ml tissue bath using a Phipps-Bird Linear Motion Transducer model ST-2. Tissues were allowed to respond to a stable maximum, at which point they were washed and allowed to return to baseline condition. All determinations are an average of at least three individual tissues at each reported dose. Data for analogs were compared to the dose response obtained for a natural PG in a given tissue. For purposes of potency comparisons, a standard dose of natural PG was selected; and all responses were calculated as a percentage of its response. Additional data were recorded as minimum effective dose (MED) and a consistently effective dose (CED) to establish compound detection levels for each tissue. A standard equivalent dose (SED) was determined. This value was defined as the amount of compound (ng/ml) which yielded a response that was equivalent to the tissue's response to a given dose of standard PG.

Guinea Pig Ileum: The ileum was dissected from 200–300 g male guinea pigs sacrificed by cervical dislocation. The tissue was suspended in 2 ml Tyrode solution (2) at 37° C. PGE₂ (30 ng/ml and/or PGF₂α (30 ng/ml) were used to establish tissue activity.

2. Hale, L.J. ed. Biol. Lab Data. p. 92, 1958.

Guinea Pig Uterus (3): Nulliparous females (300–400 g) which were not in estrus were sacrificed by cervical dislocation. The dissected uteri were incubated in 2 ml of a modified Krebs solution (4) at 37° C. Uterine activity was established using PGE₂ (1.0 ng/ml) and/or PGF₂α (10 ng/ml).

3. Clegg, P. C., P. Hopkinson and V.R. Pickles. J. Physiol. 167:1, 1963.
4. W. S. Umbreit, R. H. Burris and J. F. Stauffer. Monometric Techniques 148, 1957.

EXAMPLE 1

Dimethyl 2-oxo-3-phenylpropylphosphonate (2a):

A solution of 6.2 g (50 moles) dimethyl methylphosphonate (Aldrich) in 125 ml dry tetrahydrofuran was cooled to −78° in a dry nitrogen atmosphere. To the stirred phosphonate solution was added 21 ml of 2.37 M n-butyllithium in hexane solution (Alfa Inorganics, Inc.) dropwise over a period of 18 minutes at such a rate that the reduction temperature never rose above −65°.

After an additional 5 minutes stirring at −78°, 7.5 g (50.0 mole) methyl phenylacetate was added dropwise at a rate that kept the reaction temperature less than −70° (20 minutes). After 3.5 hours at −78°, the reaction mixture was allowed to warm to ambient temperature, neutralized with 6 ml acetic acid and rotary evaporated (water aspirator) to a white gel. The gelatinous material was taken up in 75 ml water, the aqueous phase extracted with 100 ml portions of chloroform (3x), the combined organic extracts were backwashed (50 cc H₂O), dried (MgSO₄), and concentrated (water aspirator) to a crude residue and distilled, b.p. 134°–5° (<0.1 mm) to give 3.5 g (29% dimethyl 2-oxo-3-phenylpropylphosphonate (2a).

The nmr spectrum (CDCl₃) showed a doublet centered at 3.72 δ(J = 11.5 cps, 6H) for

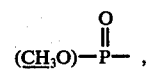

a doublet centered at 3.14 δ(J = 23 cps, 2H)

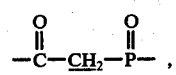

a singlet at 3.88 δ (2H) for

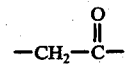

and a broad singlet at 7.22 δ (5H) for C₆H₅—.

| Additional Compounds Prepared |
| --- |

$$Ar'(CH_2)_nCCH_2P(OCH_3)_2$$
(with two C=O groups)

| Ar' | n | b.p. |
| --- | --- | --- |
| o-tolyl | 1 | 160° (0.1 mm) |
| m-tolyl | 1 | 158–162° (0.4mm) |
| p-tolyl | 1 | 145–147° (<0.2mm) |
| p-methoxyphenyl | 1 | 167–195° (0.2–0.3mm) |
| 3,4-dimethoxyphenyl | 1 | crude |
| p-chlorophenyl | 1 | 145–147° (0.2mm) |
| 3,4-dichlorophenyl | 1 | 185–188° (0.2 mm) |
| p-biphenyl | 1 | m.p. 56–58° (a) |
| o-biphenyl | 1 | (a) |
| p-tert-butylphenyl | 1 | 180° (0.2 mm) |
| α-naphthyl | 1 | 100–115° (0.05 mm) |
| β-naphthyl | 1 | 130–135° (0.04mm) |
| phenyl | 2 | 168–170° (2.0 mm) |
| phenyl | 3 | 185–190° (0.5 mm) |
| phenyl | 4 | 168° (0.5 mm) |
| 2,6-dichlorophenyl | 2 | 175 (0.1 mm) |

(a) Purified by column chromatography

EXAMPLE 2

2-[3α-Phenylbenzoyloxy-5α-hydroxy-2β-(3-oxo-4-phenyl-trans-1-buten-1-yl) cyclopent-1α-yl]Acetic Acid, γ-lactone (3a):

Method A:

Dimethyl 2-oxo-3-phenylpropylphosphonate (2a) (3.4 g., 14.2 mole) in 200 ml anhydrous ether was treated with 5.0 ml (12.5 mole) 2.5 M n-butyllithium in n-butyllithium in n-hexane (Alfa Inorganics, Inc.) in a dry nitrogen atmosphere at room temperature. After 5 min. of stirring, an additional 400 ml. of anhydriys ether was added followed by 3.85 g (11 mole) 2 -[3α-p-phenylbenzoyloxy-5α-hydroxy-2β-formylcyclopentan-1α-yl]acetic acid, γ-lactone in one portion and 50 ml anhydrous ether. After 35 minutes the reaction mixture was quenched with 5 ml glacial acetic acid, washed with 100 ml saturated sodium bicarbonate solution (4x), 100 ml water (2 x), 100 ml saturated brine (1 x ), dried (MgSO₄) and evaporated to yield 2.908 g (57%) 2-[3α-p-phenylbenzoyloxy-5α-hydroxy-2β-(3-oxo-4-phenyl-trans-1-buten-1-yl) cyclopent-1α-yl]acetic acid, γ-lactone (3a ) as a foam after column chromatography (silica gel, Baker, 60–200 mesh).

Method B:

Dimethyl 2-oxo-3-phenylpropylphosphonate (2a) (2.9 g., 12 mole) in 20 ml anhydrous dimethoxyethane was treated with 4.7 ml. (11 mole) 2.34 M n-butyllithium in n-hexane (Alfa Inorganics, Inc.) in a dry nitrogen atmosphere at room temperature. After 40 min. of stirring, 3.5 g (10 mole) 2-[3α-p-phenylbenzoyloxy-5α-hydroxy-2β-formylcyclopentan-1α-yl]acetic acid, α-lactone was added in one portion followed by 15 ml anhydrous 1,2-dimethoxy ethane. After 30 minutes the reaction mixture was quenched with 1 ml. glacial acetic acid, filtered, washed with 20 ml. saturated sodium bicarbonate solution (2 x), 20 ml. saturated brine (1 x ), dried (Na₂SO₄) and evaporated to yield 2 g (43%) 2-[3α-p-phenylbenzoyloxy-5α-hydroxy-2β-(3-oxo-4-phenyl-trans-1-buten-1-yl)cyclopent-1α-yl]acetic acid, γ-lactone (3a) as a Foam after column chromatography (silica gel, Baker, 60–200 mesh).

Method C:

To a suspension of 464 mg. of 75% dispersion of sodium hydride in 40 ml. of tetrahydrofuran is added dropwise 2.9 g. (12 mole) of dimethyl 2-oxo-3-phenylpropylphosphonate (2a). The mixture is stirred for 45 minutes then a slurry of 3.5 g. (10 moles) 2-[3α-p-phenylbenzoyloxy-5α-hydroxy-2β-formylcyclopent-1α-yl]acetic acid, γ-lactone in 10 ml. of tetrahydrofuran is added. The reaction is stirred for 1 hour then is quenched (pH ~5) by addition of acetic acid. The mixture is then concentrated, the residue is dissolved in ethyl acetate, and the organic layer is washed with water, saturated sodium bicarbonate, and saturated brine, is dried (anhydrous magnesium sulfate), and is concentrated. Purification of the crude product by column chromatography provides the desired 2-[3α-p-phenylbenzoyloxy-5α-hydroxy-2β-(3-oxo-4-phenyl-trans-1-buten-1-yl) cyclopent-1α-yl]acetic acid, γ-lactone.

The ir spectrum (CHCL₃) of the product (3a) exhibited adsorption bands at 1775 cm⁻¹ (strong), 1715 cm⁻¹ (strong), 1675 cm⁻¹ (medium) and 1630 cm⁻¹ (medium) attributable to the carbonyl groups and at 973 cm⁻¹ for the trans double bond. The nmr spectrum (CDCl₃) exhibited a multiplet at 7.23–8.18δ (9H) for the p-biphenyl group, a doublet of doublets centered at 6.75 δ (1H, J = 16 cps) and a doublet centered at 6.27 (1H, J = 16 cps) for the olefinic protons, a broad singlet at 7.20 δ (5H) for

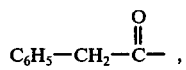

a singlet at 3.84 (2H) for

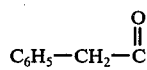

and multiplets at 4.90–5.50 δ (2H) and 2.21–3.07 (6H) for the remainder of the protons.

Additional Compounds Prepared

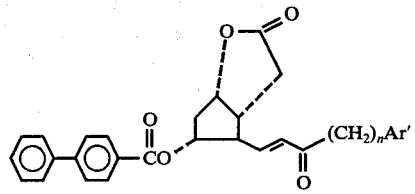

| Ar' | n | method | m.p. |
|---|---|---|---|
| o-tolyl | 1 | B | 120–122° |
| p-tolyl | 1 | B | 145–146° |
| p-methoxyphenyl | 1 | A | 136–139° |
| 3,4-dimethoxyphenyl | 1 | C | oil |
| p-biphenyl | 1 | B | 186–187° |
| p-chlorophenyl | 1 | B | 103–112° |
| α-naphthyl | 1 | B | oil |
| β-naphthyl | 1 | C | 120–128° |
| phenyl | 2 | B | 129–129.5° |
| phenyl | 3 | B | 139–140° |

EXAMPLE 3

2-[3α-p-Phenylbenzoyloxy-5α-hydroxy-2β-(3α-hydroxy-4-phenyltrans-1-buten-1yl) cyclopent-1α-yl]acetic acid, γ-lactone (4a) and 2-[3α-n-Phenylbenzoyloxy-5α-hydroxy-2β (3β-hydroxy-4-phenyltrans-1-buten-1-yl) cyclopent-1α-yl]acetic acid γ- lactone (5a)-MethoA To a solution of 2908 mg (6.2 mole) 2- [3α-p-phenylbenzoyloxy-5α-hydroxy-2β-(3oxo-4-phenyl-trans-1-buten-1-yl) cyclopent-1α-yl]acetic acid, γ-lactone (3a) in 30 ml dry 1,2-dimethoxyethane in a dry nitrogen atmosphere at ambient temperature was added dropwise 2.0 ml. of a 1.0 M zinc borohydride solution in 1,2-dimethyoxyethane. After stirring at 0° for 2 hours, a saturated sodium bitartrate solution was added dropwise until hydrogen evolution ceased. The reaction mixture was allowed to stir for 5 minutes at which time 250 ml dry methylene chloride was added. After drying (MgSO₄) and concentrating (water aspirator) the resultant semisolid was purified by column chromatography on silica gel (Baker "Analyzed" Reagent 60–200 mesh) using ether as eluent. After elution of less polar impurities a fraction containing 658 mg 2 -[3α-p-phenylbenzoyloxy-5α-hydroxy-2β-(3α-hydroxy-4-phenyl-trans-1-buten-1-yl) cyclopent-1α-yl]acetic acid, γ-lactone) (4a), a 480 mg fraction of mixed 4a and 5a and finally a fraction (671 mg) of 2-[3α-p-phenylbenzoyloxy-5α-hydroxy-2β-(3β-hydroxy-4-phenyl-trans-1-buten-yl) cyclopent-1α-yl]acetic acid, γ-lactone (5a).

The ir spectrum (CHCl₃) of 4a and 5a had a strong carbonyl adsorptions at 1770 and 1715 cm⁻¹ and an adsorption at 970 cm⁻¹ for the trans double bond. The NMR spectrum (CDCl₃) of 4a and 5a was consistent with the assigned structure.

Method B

To a solution of 2.91 g (6.2 mole) 2[3α-p-phenylbenzoyloxy-5α-hydroxy-2β-(3-oxo-4-phenyl-trans-1-buten-1-yl) cyclopent-1α-yl] acetic acid, γ-lactone (3a) in 100 ml of tetrahydrofuran, cooled to −78°, is added 6.2 ml of a 1.0 M solution of lithium triethylborohydride in tetrahydrofuran (Aldrich). The solution is stirred in the cold for 30 minutes then is quenched by the addition of 5 ml of a 9:1 mixture of water:acetic acid. The quenched mixture is let warm then is concentrated. The residue is dissolved in ethyl acetate and the organic layer is washed with water, saturated sodium bicarbonate, and saturated brine, is dried (anhydrous magnesium sulfate), and is concentrated. Purification of the crude product by column chromatography affords pure 4a and 5a.

Additional Compounds Prepared

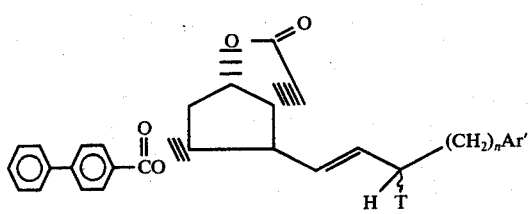

| Ar' | n | T | Mobility[a] |
|---|---|---|---|
| o-tolyl | 1 | αOH | L.P. |
| o-tolyl | 1 | βOH | M.P. |
| p-tolyl | 1 | αOH | L.P. |
| p-tolyl | 1 | βOH | M.P. |
| p-methoxyphenyl | 1 | αOH | L.P. |
| p-methoxyphenyl | 1 | βOH | M.P. |
| 3,4-dimethoxyphenyl | 1 | αOH | L.P. |
| 3,4-dimethoxyphenyl | 1 | βOH | M.P. |
| p-biphenyl | 1 | αOH | L.P. |
| p-biphenyl | 1 | βOH | M.P. |
| p-chlorophenyl | 1 | αOH | L.P. |
| p-chlorophenyl | 1 | βOH | M.P. |
| α-naphthyl | 1 | αOH | L.P. |
| α-naphthyl | 1 | βOH | M.P. |
| β-naphthyl | 1 | αOH | L.P. |
| β-naphthyl | 1 | βOH | M.P. |
| phenyl | 2 | αOH | L.P. |
| phenyl | 2 | βOH | M.P. |
| phenyl | 3 | αOH | L.P. |
| phenyl | 3 | βOH | M.P. |

[a]Determined by TLC; M.P. = more polar; L.P. = less polar.

EXAMPLE 4

2[3α,5α-Dihydroxy-2β-(3α-hydroxy-4-phenyl-trans-1-buten-1yl) cyclopent-1αyl]acetic acid, γ-lactone (6a):

A heterogeneous mixture of 658 mg (1.35 mole) of 2-[3α-p-phenylbenzoyloxy-5α-hydroxy-2β-(3α-hydroxy-4-phenyl-trans-1-buten-1-yl) cyclopent-1α-yl]acetic acid, γ-lactone (4a), 7.1 ml. of absolute methanol and 188 mg. of finely powdered, anhydrous potassium carbonate was stirred at room temperature for one hour, then cooled to 0°. To the cooled solution was added 2.8 ml (2.8 mole) of 1.0N aqueous hydrochlordide acid. After stirring at 0° for an additional 10 minutes, 5 ml. of water was added with concomitant formation of methyl p-phenylbenzoate which was collected by filtration. The filtrate was saturated with solid sodium chloride, extracted with ethyl acetate (4 × 10 ml.), the combined organic extracts were washed with saturated sodium bicarbonate (10 ml.), dried (MgSO₄) and concentrated to give 381 mg of viscous, oily 2-[3α,-5α-dihydroxy-2β-(3α-hydroxy-4-phenyl-trans-1-buten-1-yl) cyclopent-1α-yl]acetic acid, γ-lactone (6a).

The ir spectrum (CHCl₃) exhibited a strong adsorption at 1770 cm⁻¹ for the lactone carbonyl and medium adsorption at 965 cm—¹ for the trans-double bond.

Additional Compounds Prepared

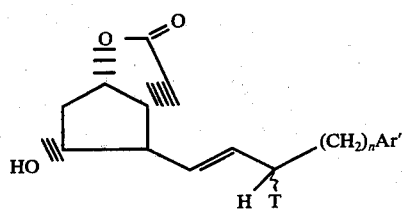

| Ar' | n | T |
|---|---|---|
| phenyl | 1 | βOH |
| o-tolyl | 1 | αOH |
| o-tolyl | 1 | βOH |
| p-tolyl | 1 | αOH |
| p-methoxyphenyl | 1 | αOH |
| p-methoxyphenyl | 1 | βOH |
| 3,4-dimethoxyphenyl | 1 | αOH |
| p-biphenyl | 1 | αOH |
| p-biphenyl | 1 | βOH |
| p-chlorophenyl | 1 | αOH |
| α-naphthyl | 1 | αOH |
| α-naphthyl | 1 | βOH |
| β-naphthyl | 1 | αOH |
| β-naphthyl | 1 | βOH |
| phenyl | 2 | αOH |
| phenyl | 2 | βOH |
| phenyl | 3 | αOH |
| phenyl | 3 | βOH |

EXAMPLE 5

2-[5α-Hydroxy-3α-(tetrahydropyran-2-yloxy)-2β-(3α-[tetrahydropyran-2-yloxy]-4-phenyl-trans-1-buten-1-yl)cyclopent-1α-yl]acetic acid, γ-lactone (7a):

To a solution of 38 mg (1.33 mmole) 2-[3α,5α-dihydroxy-2β-(3α-hydroxy-4-phenyl-trans-1-buten-yl)cyclopent-1α-yl]acetic acid, γ-lactone (6a) in 5 ml anhydrous methylene chloride and 0.4 ml of 2,3-dihydropyran at 0° in a dry nitrogen atmosphere was added 5 mg p-toluenesulfonic acid monohydrate. After stirring for 15 minutes, the reaction mixture was combined with 100 ml ether, the ether solution washed with saturated sodium bicarbonate (1 × 15 ml) then saturated brine (1 × 15 ml), dried (MgSO₄) and concentrated to yield 615 mg (>100%) crude 2-[5α-hydroxy-3α-(tetrahydropyran-2-yloxy)-2β-(3α-[tetrahydropyran-2-yloxy]-4-phenyl-trans-1-buten-1-yl)cyclopent-1α-yl]acetic acid, γ-lactone (7a).

Additional Compounds Prepared

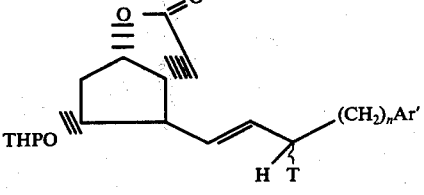

| Ar' | n | T |
|---|---|---|
| phenyl | 1 | βOTHP |
| o-tolyl | 1 | αOTHP |
| o-tolyl | 1 | βOTHP |
| p-tolyl | 1 | αOTHP |
| p-methoxyphenyl | 1 | αOTHP |
| p-methoxyphenyl | 1 | βOTHP |
| 3,4-dimethoxyphenyl | 1 | αOTHP |
| p-biphenyl | 1 | αOTHP |
| p-biphenyl | 1 | βOTHP |
| p-chlorophenyl | 1 | αOTHP |
| α-naphthyl | 1 | αOTHP |
| α-naphthyl | 1 | βOTHP |
| β-naphthyl | 1 | αOTHP |

-continued

Additional Compounds Prepared

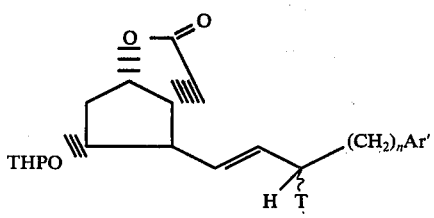

| Ar' | n | T |
|---|---|---|
| β-naphthyl | 1 | βOTHP |
| phenyl | 2 | αOTHP |
| phenyl | 2 | βOTHP |
| phenyl | 3 | αOTHP |
| phenyl | 3 | βOTHP |

EXAMPLE 6

2-[5α-Hydroxy-3α-(tetrahydropyran-2-yloxy)-2β-(3α-[tetrahydropyran-2-yloxy]-4-phenyl-trans-1-buten-1yl)-cyclopent-1α-yl]acetaldehyde, γ-hemiacetal (8a):

A solution of 605 mg (1.33 mmole) 2-[5α-hydroxy-3α-(tetrahydropyran-2-yloxy)-2β-3α-[tetrahydropyran-2-yloxy]-4-phenyl-trans-1-buten-1-yl)cyclopent-1α-yl]acetic acid, γ-lactone (7a) in 8 ml dry toluene was cooled to −78° in a dry nitrogen atmosphere. To this cooled solution was added 3.0 ml of 20% diisobutylaluminum hydride in n-hexane (Alfa Inorganics) dropwise at such a rate so that the internal temperature never rose above −65° (15 minutes). After an additional 45 minutes of stirring −78°, anhydrous methanol was added until gas evolution ceased and the reaction mixture was allowed to warm to room temperature. The reaction mixture was combined with 100 ml ether, washed with 50% sodium potassium tartrate solution (4 × 20 ml), dried (Na$_2$SO$_4$) and concentrated to yield 615 mg (100%) 2-[5α-hydroxy-3α-(tetrahydropyran-2-yloxy)-2β-(3α-[tetrahydropyran-2-yloxy)-4-phenyl-trans-1-buten-1-yl)cyclopent-1-yl]acetaldehyde, γ-hemiacetal (8a).

Additional Compounds Prepared

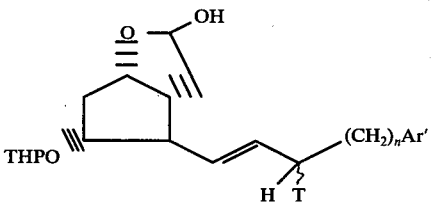

| Ar' | n | T |
|---|---|---|
| phenyl | 1 | βOTHP |
| o-tolyl | 1 | αOTHP |
| o-tolyl | 1 | βOTHP |
| p-tolyl | 1 | βOTHP |
| p-methoxyphenyl | 1 | αOTHP |
| p-methoxyphenyl | 1 | βOTHP |
| 3,4-dimethoxyphenyl | 1 | αOTHP |
| p-biphenyl | 1 | αOTHP |
| p-biphenyl | 1 | βOTHP |
| p-chlorophenyl | 1 | αOTHP |
| α-naphthyl | 1 | αOTHP |
| α-naphthyl | 1 | βOTHP |
| β-naphthyl | 1 | αOTHP |
| β-naphthyl | 1 | βOTHP |
| phenyl | 2 | αOTHP |
| phenyl | 2 | βOTHP |
| phenyl | 3 | αOTHP |
| phenyl | 3 | βOTHP |

EXAMPLE 7

9α-Hydroxy-11α,15α-bis-(tetrahydropyran-2-yloxy)-16-phenyl-cis-5-trans-13-ω-tetranor prostadienoic acid (9a):

To a solution of 1760 mg (4.0 mmole) (4-carbohydroxy-n-butyl) triphenylphosphonium bromide in a dry nitrogen atmosphere in 5.0 ml dry dimethyl sulfoxide was added 3.2 ml (7.0 mmole) of a 2.2M solution of sodium methylsufinylmethide in dimethyl sulfoxide. To this red ylide solution was added dropwise a solution of 615 mg (1.34 mmole) 2-[5α-hydroxy-3α-(tetrahydropyran-2-yloxy)-2β-(3α-]tetrahydropyran-2-yloxy]-4-phenyl-trans-1-buten-1-yl)cyclopent-* 1α-yl]acetaldehyde, γ-hemiacetal (8a) in 5.0 ml dry dimethyl sulfoxide over a period of 20 minutes. After an additional 2 hours stirring at room temperature, the reaction mixture was poured into ice water. The basic aqueous solution was washed twice with ethyl acetate (20 ml.) and acidified to pH∼3 with 10% aqueous hydrochloric acid. The acidic solution was extracted with ethyl acetate (3 × 20 ml) and the combined organic extracts washed once with water (10 ml.), dried (MgSO$_4$) and evaporated to a solid residue. This solid residue was triturated with ethyl acetate and filtered. The filtrate was purified by column chromatography on silica gel (Baker "Analyzed" Reagent 60–200 mesh) using ethyl acetate as eluent. After removal of high R$_f$ impurities, 150 mg of 9α-hydroxy-11α,15α-bis-(tetrahydropyran-2-yloxy)-16-phenyl-cis-5-trans-13-ω-tetranor prostadienoic acid (9a) was collected.

Additional Compounds Prepared

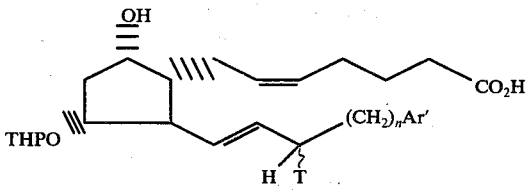

| Ar' | n | T |
|---|---|---|
| phenyl | 1 | βOTHP |
| o-tolyl | 1 | αOTHP |
| o-tolyl | 1 | βOTHP |
| p-tolyl | 1 | αOTHP |
| p-methoxyphenyl | 1 | αOTHP |
| p-methoxyphenyl | 1 | βOTHP |
| 3,4-dimethoxyphenyl | 1 | αOTHP |
| p-biphenyl | 1 | αOTHP |
| p-biphenyl | 1 | βOTHP |
| p-chlorophenyl | 1 | αOTHP |
| α-naphthyl | 1 | αOTHP |
| α-naphthyl | 1 | βOTHP |
| β-naphthyl | 1 | αOTHP |
| β-naphthyl | 1 | βOTHP |
| phenyl | 2 | αOTHP |
| phenyl | 2 | βOTHP |
| phenyl | 3 | αOTHP |
| phenyl | 3 | βOTHP |

EXAMPLE 8

9-Oxo-11α,15α-bis-(tetrahydropyran-2-yloxy)-16-phenyl-cis-5-trans-13-ω-tetranor prostadienoic acid (10a):

To a solution cooled to −10° under nitrogen of 2300 mg (4.24 mmole) 9α-hydroxy-11α,15α-bis-(tetrahydropyran-2-yloxy)-16-phenyl-cis-5-trans-13-ω-tetranor prostadienoic acid (9a) in 50 ml. reagent grade acetone was added dropwise to 11.3 ml. (29.6 mmole) of Jone's reagent. After 20 minutes at −10°, 10 ml. 2-propanol was added and the reaction mixture was allowed to stir an additional 5 minutes at which time it was combined with 300 ml. ethyl acetate, washed with water (3 × 50 ml.), dried (MgSO₄) and concentrated to give 1983 mg. of 9-oxo-11α,15α-bis-(tetrahydropyran-2-yloxy)-16-phenyl-cis-5-trans-13-ω-tetranor prostadienoic acid (10a).

Additional Compounds Prepared

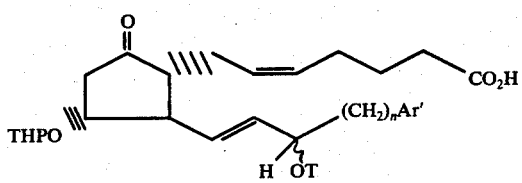

| Ar' | n | T |
|---|---|---|
| phenyl | 1 | βOTHP |
| o-tolyl | 1 | αOTHP |
| o-tolyl | 1 | βOTHP |
| p-tolyl | 1 | αOTHP |
| p-methoxyphenyl | 1 | αOTHP |
| p-methoxyphenyl | 1 | βOTHP |
| 3,4-dimethoxyphenyl | 1 | αOTHP |
| p-biphenyl | 1 | αOTHP |
| p-biphenyl | 1 | βOTHP |
| p-chlorophenyl | 1 | αOTHP |
| α-naphthyl | 1 | αOTHP |
| α-naphthyl | 1 | βOTHP |
| β-naphthyl | 1 | αOTHP |
| β-naphthyl | 1 | βOTHP |
| phenyl | 2 | αOTHP |
| phenyl | 2 | βOTHP |
| phenyl | 3 | αOTHP |
| phenyl | 3 | βOTHP |

EXAMPLE 9

9-Oxo-11α,15α-dihydroxy-16-phenyl-cis-5-trans-13-ω-tetranor-prostadienoic acid (11a):

A solution of 1637 mg. (3.02 mmole) 9-oxo-11α,15α-bis-tetrahydropyran-2-yloxy)-16-phenyl-cis-5-trans-13-ω-tetranor-prostadienoic acid (10a) in 20 ml. of a 65:35 mixture of glacial acetic acid: water was stirred under nitrogen at room temperature for 24 hours and then was concentrated by rotary evaporation. The resultant crude oil was purified by column chromatography on silica gel (Mallinckrodt CC-4 100–200 mesh) using ethyl acetate-cyclohexane as eluent. After elution of less polar impurities, the oily 9-oxo-11α,15α-dihydroxy-16-phenyl-cis-5-trans-13-ω-tetranor-prostadienoic acid (11a) weighing 365 mg. was collected. Biological activity: guinea pig uterus 3 guinea pig ileum 1, guinea pig Histamine aerosol test 100, dog blood pressure 300–400

Additional Compounds Prepared

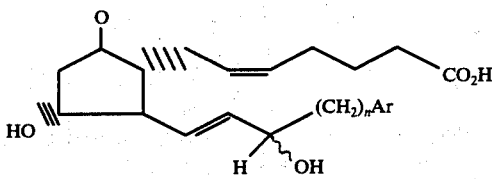

| Ar | n | T | M.P. |
|---|---|---|---|
| p-biphenyl | 1 | αOH | oil |
| p-biphenyl | 1 | βOH | solid |
| α-naphthyl | 1 | αOH | oil |
| α-naphthyl | 1 | βOH | oil |
| β-naphthyl | 1 | αOH | oil |
| β-naphthyl | 1 | βOH | oil |

EXAMPLE 10

9α,11α,15α-Trihydroxy-16-phenyl-cis-5-trans-13-ω-tetranor-prostadienoic acid (12a):

A mixture of 0.7 g of 9α-hydroxy-11α,15α-bis-(tetrahydropyran-2-yloxy)-16-phenyl-cis-5-trans-13-ω-tetranorprostadienoic acid (9a) in 5 ml. of a 65:35 mixture of acetic acid: water was stirred under nitrogen at room temperature overnight, then was concentrated under reduced pressure to a viscous oil. The crude product was purified by column chromatography on Mallinckrodt CC-4 silica gel using ethyl acetate as eluent. After elution of less polar impurities, the desired 9α,11α,15α-trihydroxy-16-phenyl-cis-5-trans-13-ω-tetranor-prostadienoic acid (12a) was obtained as a viscous, colorless oil weighing 51 mg.

The ir spectrum (CHCl₃) of 12a showed a strong absorption at 1710 cm⁻¹ for the carbonyl group and a medium absorption at 970 cm⁻¹ for the trans double bond.

The product obtained above (12a) may be converted to 16-phenyl-ω-tetranor prostaglandin F₁α via the process of Example 13. 12a may also be converted to 16-phenyl-ω-tetranor prostaglandin F₀α, via the process of Example 12.

Additional Compounds Prepared

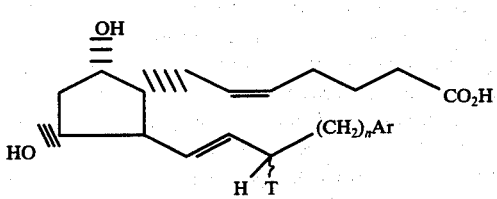

| Ar | n | T | M.P. |
|---|---|---|---|
| p-biphenyl | 1 | αOH | solid |
| α-naphthyl | 1 | αOH | oil |
| α-naphthyl | 1 | βOH | oil |
| β-naphthyl | 1 | αOH | oil |
| β-naphthyl | 1 | βOH | oil |

EXAMPLE 11

9-oxo-15α-hydroxy-16-(β-naphthyl)-cis-5-Δ¹⁰,¹¹-trans-13-ω-tetranorprostatrienoic acid (15b):

A solution of 50 mg of 9-oxo-11α,15α-dihydroxy-16-(β-naphthyl)-cis-5-trans-13 -ω-tetranor-prostadienoic acid (11b) in 10 ml dry methylene chloride and 10 ml formic acid is stirred at room temperature for 5 hours. The reaction mixture is diluted with 50 ml toluene and evaporated to yield (after chromatography) 9-oxo-11α-hydroxy-16-(β-naphthyl)-cis-5-Δ¹⁰,¹¹-trans-13-ω-tetranor prostadienoic acid (15b).

In the same way 15-substituted-ω-pentanor prostaglandins of the A₂, A₁, A₀ and 13,14 dihydro A₂ series may be prepared from 15 -substituted-ω-pentanorprostaglandins of the E₂, E₁, E₀ and 13,14-dihydro series respectively.

EXAMPLE 12

9-Oxo-11α,15α-dihydroxy-16-(β-naphthyl)-ω-tetranor prostanoic acid (28b):

A heterogeneous solution of 34 mg 9-oxo-11α,15α-dihydroxy-16-(β-naphthyl)-cis-5-trans-13-ω-tetranor prostadienoic acid (11a) and 13 mg of 5% palladium on carbon in 3 ml. absolute methanol is hydrogenated (1 atm) at 0° for 2 hours. The reaction mixture is filtered and evaporated to yield 9-oxo-11α,15α-dihydroxy-16-(β-naphthyl)-ω-tetranor prostanoic acid (28b).

In the same way 15-substituted-ω-pentanorprostaglandins of the $E_o$, $F_{o\alpha}$, and $F_{o\beta}$ series may be prepared from 15-substituted-ω-pentanorprostaglandins of the $E_1$, $F_{1\alpha}$, $F_{1\beta}$, $E_2$, $F_{2\alpha}$, $F_{2\beta}$, and 13,14-dihydro $E_2$, $F_{2\alpha}$ and $F_{2\beta}$ series respectively.

EXAMPLE 13

9-oxo-11α,15α-dihydroxy-16-(p-biphenyl)-trans-13-ω-tetranorprostenoic acid (29a):

A solution of 50 mg 9-oxo-11α,15α-dihydroxy-16-p-biphenylcis-5-trans-13-ω-tetranorprostadienoic acid (11c) in 5 ml of dry ether is treated with 448 mg (3.6 mmole) dimethyl isopropyl chlorosilane and 360 mg (3.6 mmole) triethylamine at 25° for 48 hours. The reaction mixture is cooled to 0°, methanol was added and the resulting solution is washed with water (3 × 2 ml), dried (MgSO$_4$) and evaporated. The crude residue is then taken up in 6 ml methanol and 30 mg of 50% Pd/C and the resultant slurry is hydrogenated for 4 hours at −22° (CCl$_4$/Dry Ice). After filtration through super cell and evaporation, the hydrogenated product is hydrolyzed in 2 ml of acetic acid-water (3:1) for 10 minutes, diluted with water (20 ml) and extracted with ethyl acetate (4 × 15 ml). The combined organic extracts are washed with water (2 × 10 ml), dried (MgSO$_4$) and evaporated to yield 9-oxo-11α,15α-dihydroxy-16-p-biphenyl-trans-13-ω-tetranorprostenoic acid (29c).

In the same way 15-substituted-ω-pentanorprostaglandins of the $E_1$, $F_{1\alpha}$, and $F_{1\beta}$ series may be prepared from 15-substituted -ω-pentanorprostaglandins of the $E_2$, $F_{2\alpha}$, and $F_{2\beta}$ series.

EXAMPLE 14

9-Beta,11-alpha,15-alpha-trihydroxy-16-(beta-naphthyl)-cis-5-trans-13-ω-tetranorprostadienoic acid To a solution, cooled to 0°, of 100 mg. of 9-oxo-11-alpha,15-alpha-dihdyroxy-16-(beta-naphthyl)-cis-5-trans-13-ω-tetranorprostadienoic acid in 10 ml. of methanol is added a cooled solution of 300 mg. of sodium borohydride in 35 ml. of methanol. The solution is stirred at 0° for 35 minutes, 2 ml. of water is added, and the mixture is concentrated. The residue is overlaid with ethyl acetate and the aqueous layer is acidified to pH ∼ 3 with 10% hydrochloric acid. The aqueous layer is extracted with ethyl acetate and the combined organic extracts are washed with water and saturated brine, are dried (anhydrous magnesium sulfate), and concentrated. Purification of the residue by column chromatography provides 9-alpha,11-alpha,15-alpha-trihydroxy-16-(betanaphthyl)-cis-5-trans-13-ω-tetranorprostadenoic acid and 9-beta,11-alpha,15-alpha-trihydroxy-16-(beta-naphthyl)-cis-5-trans-13-ω-tetranorprostadenoic acid.

In the same way 15-substituted-ω-pentanorprostaglandins of the $F_{2\text{-}beta}$, $F_{1\text{-}beta}$, $F_{o\text{-}beta}$, and 13,14-dihydro $F_{2\text{-}beta}$ series may be prepared from 15-substituted-ω-pentanorprostaglandins of the $E_2$, $E_1$, $E_o$, and 13,14-dihydro $E_2$ series respectively.

EXAMPLE 15

2-[2-Beta-benzyloxymethyl-3-alpha-(tetrahydropyran-2-yloxy)-5-alpha-hydroxy-cyclopent-12-yl]acetaldehyde, gamma-hemiacetal To a stirred solution, cooled to −78°, of the known 2-[2-beta-benzyloxymethyl-3-alpha-(tetrahydropyran-2-yloxy-5-alpha-hydroxycyclopent-12-yl]acetic acid, gamma-lactone in 78.8 ml. of toluene was added 13.4 ml. (10.8 mmoles) of a 0.805M solution of diisobutylaluminum hydride in hexane dropwise. The solution was stirred in the cold under nitrogen for 1.0 hour then was quenched by the dropwise addition of methanol until gas evolution ceased. The quenched mixture was warmed to room temperature, was diluted with ether (79 ml.), was washed with 50% sodium potassium tartrate (3x) and saturated brine (1x), was dried (anhydrous magnesium sulfate, and was concentrated to afford the crude, colorless, oily 2-[2-beta-benzyloxymethyl-3-alpha-(tetrahydropyran-2-yloxy)-5-alpha-hydroxycyclopent-1-alpha-yl]acetaldehyde, gamma-hemiacetal weighing 3.15 g. (92.0% yield). The ir, nmr, and mass spectra of the oil were consistent with the assigned structure.

EXAMPLE 16

7-[2-Beta-Benzyloxymethyl-3-alpha-(tetrahydropyran-2-yloxy)-5-alpha-hydroxycyclopent-1-alpha-yl]-cis-5-heptenoic acid To a solution of 4.96 g. (11.2 mmoles) of 4-carbohydroxy-n-butyl)triphenyl-phosphonium bromide in 8.85 ml. of dimethyl sulfoxide was added dropwise 9.73 ml. (21.2 mmoles) of a 2.18 M solution of sodium methylsulfinylmethide in dimethyl sulfoxide. To the resultant red ylide solution was added dropwise over a period of 1.0 hour a solution of 1.57 g. (4.50 mmoles) of the crude hemiacetal prepared in Example 15 in 13.7 ml. of dimethyl sulfoxide. After being stirred for an additional 45 minutes the reaction was poured onto ice-water. The basic aqueous solution was extracted with a 2:1 mixture of ethyl acetate: ether (2 × 60 ml.), was then covered with ethyl acetate, and was acidified with 1.0 N hydrochloric acid to ph ∼ 3. The aqueous layer was extracted further with ethyl acetate; the combined ethyl acetate extracts were washed with water, were dried (anhydrous magnesium sulfate), and were concentrated to a viscous yellow oil. The crude oil was purified by chromatography on 30 g. of silica gel using ethyl acetate as eluent. After elution of high $R_f$ impurities the desired 7-[2-beta-benzyloxymethyl-3-alpha-(tetrahydropyran-2-yloxy)-5-alpha-hydroxycyclopent-1-alpha-yl]-cis-5-heptenoic acid was collected weighing 1.75 g. (90.0% yield).

EXAMPLE 17

Methyl 7-[2-beta-benzyloxymethyl-3-alpha-(tetrahydropyran-2-yloxy)-5-alpha-hydroxycyclopent-1-alpha-yl]-cis-5-heptenoate A solution of 1.75 g. (4.06 mmoles) of the chromatographed acid prepared in Example 16 in 17.5 ml. of anhydrous ether was titrated at room temperature with an ethereal diazomethane solution until the yellow color persisted for 5 minutes. The reaction was then decolorized by the dropwise addition of glacial acetic acid. The ethereal solution was then washed with saturated sodium bicarbonate (IX) and saturated brine (IX), was dried (anhyrous magnesium sulfate), and was concentrated to afford the faintly yellow, oily methyl 7-[2-beta-benzyloxymethyl-3-alpha-(tetrahydropyran-2-yloxy)-5-alpha-hydroxycyclopent-1-alpha-yl]-cis-5-heptenoate weighing 1.80 g. (99.0% yield).

EXAMPLE 18

Methyl 7-[2-beta-benzyloxymethyl-3-alpha(tetrahydropyran-2-yloxy)-5-alpha-acetoxycyclopent-1-alpha-yl]-cis-5-heptenoate A mixture of 1.58 g. (3.54 mmoles) of the crude hydroxyester prepared in Example 17, 5.0 ml. of pyridine and 0.736 ml. (7.78 mmoles) of acetic anhyride was stirred under nitrogen at 50° overnight. The mixture was then cooled to room temperature and was diluted with ether (75 ml.). The etheral was washed with water (1x) and with saturated copper (11) sulfate (3x), was dried (anhydrous magnesium sulfate), and was concentrated to afford the colorless, oily methyl 7-[2-beta-benzyloxymethyl-3-alpha-(tetrahydropyran-2-yloxy)-5-alpha-acetoxycyclopent-1-alpha-yl]-cis-5-heptenoate weighing 1.61 g. (93.5% yield).

EXAMPLE 19

7-[2-Beta-Hydroxymethyl-3-alpha(tetrahydropyran-2-yloxy)-5-alpha-acetoxycyclopent-1-alpha-yl]heptanoate A heterogeneous mixture of 1.53 g. (3.14 mmoles) of the crude acetoxy ester prepared in Example 18, 305 mg. of 5% palladium on carbon, and 15.3 ml. of a 20:1 mixture of absolute ethanol:glacial acetic acid was stirred at room temperature under one atmosphere of hydrogen for 48 hours. The mixture was then filtered through Celite 545 and the filtrate was concentrated to afford the colorless, oily methyl 7-[2-beta-hydroxymethyl-3-alpha-(tetrahydropyran-2-yloxy)-5-alpha-acetoxycylcopentan-1-alpha-yl]heptanoate weighing 1.10 g. (87.5% yield).

EXAMPLE 20

Methyl 7-[2-beta-formyl-3-alpha(tetrahydropyran-2-yloxy)-5-alpha-acetoxycyclopent-1-alpha-yl]heptanoate To a mechanically stirred solution of 3.37 ml. (41.7 mmoles) of pyridine in 50 ml. of methylene chloride cooled to 10° to 15° under nitrogen was added portionwise over a period of 30 minutes 1.89 g. (18.9 mmoles) of chromium trioxide. The dark burgandy solution was then let warm to room temperature then was cooled to 0°. To the cold solution was added a solution of 0.947 g. (2.37 mmole) of the crude alcohol prepared in Example 19 in 7.0 ml. of methylene chloride with the concomitant formation of a dense black precipitate. The suspension was stirred in the cold for 15 minutes then 7.21 g. (52.2 mmoles) of finely ground sodium bisulfate monohydrate was added. After being stirred for 10 minutes 6.25 g. (52.2 mmoles) of anhdyrous magnesium sulfate was added. After being stirred for 5 minutes the dark suspension was filtered through a pad of Celite, was washed with methylene chloride, then was concentrated by rotary evaporation (bath < 10°) to afford the crude dark brown, oily methyl 7-[2-beta-formyl-3-alpha-(tetrahydropyran-2-yloxy)-5-alpha-acetoxycyclopent-1-alpha-yl]-heptanoate which was used without purification.

EXAMPLE 21

Methyl 9-alpha-acetoxy-11-tetrahydropyran-2-yloxy)-15-oxo-16-p-biphenyl-trans-13-ω-tetranorprostenoate To a suspension of 110 mg. (2.61 mmoles) of a 57.0% dispersion of sodium hydride in mineral oil in 20 ml. of dimethoxyethane is added 1.16 g. (2.61 mmoles) of dimethyl-2-oxo-3-p-biphenylpropylphosphonate. The mixture is stirred at room temperature for 1 hour under nitrogen with the concomitant formation of a dense white precipitate. To this suspension is added a solution of 0.947 g. (2.37 mmoles) of the crude aldehyde in 4 ml. of dimethyoxyethane. The resultant slightly turbid, brown solution is stirred at room temperature for 2.0 hours under nitrogen. The reaction is then quenched by the addition of glacial acid to pH ~ 7 and is concentrated by rotary evaporation. The resultant crude residue is slurried with benzene, filtered, and concentrated by rotary evaporation to afford the crude product. The crude product is purified by column chromatography on silica gel to provide the product, methyl 9-alpha-acetoxy-11-alpha-(tetrahydropyran-2-yloxy)-15-oxo-16-p-biphenyl-trans-13-prostenoate.

EXAMPLE 22

Methyl 9-alpha-acetoxy-11-alpha-(tetrahydropyran-2-yloxy)-15-alpha-hydroxy-16-p-biphenyl-trans-13-ω-tetranorprostenoate and Methyl 9-alpha-acetoxy-11-alpha-(tetrahydropyran-2-yloxy)-15-betahydroxy-16-p-biphenyl-trans-13-ω-tetranorprostenoate To a solution, cooled to −78°, of 1.1 g. of the ketene of Example 21 in 25 ml. of tetrahydrofuran is added 1.81 ml. of a 1.0 M solution of lithium triethylborohydride in tetrahydrofuran (Aldrich). The mixture is stirred for 30 minutes then quenched in the cold by the addition of 1 ml. of a 9:1 mixture of water-acetic acid. The solution is let warm to room temperature and concentrated. The residue is dissolved in ethyl acetate, is washed with water and saturated sodium bicarbonate, is dried (anhydrous magnesium sulfate), and is concentrated. Purification of crude residue by column chromatography provides methyl 9-alpha-acetoxy-11-alpha-(tetrahydropyran-2-yloxy)-15-alpha-hydroxy-16-p-biphenyl-trans-13-ω-tetranorprostenoate and methyl 9-alpha-acetoxy-11-alpha-(tetrahydropyran-2-yloxy)-15-beta-hydroxy-16-p-biphenyl-trans-13-ω-tetranorprostenoate.

EXAMPLE 23

Methyl 9-alpha-acetoxy-11-alpha,15-alpha-bis-(tetrahydropyran-2-yloxy)-trans-13-16-p-biphenyl-ω-tetranorprostenoate A mixture of 0.290 g. (0.510 mmole) of the product of Example 22, 0.14 ml. (1.53 mmoles) of dihydropyran, 4.2 ml. of methylene chloride, and 1 crystal of p-toluenesulfonic acid monohydrate is stirred at room temperature under nitrogen for 20 minutes. The reaction mixture is then diluted with ether, is washed with saturated aqueous sodium bicarbonate (IX), is dried (anhydrous magnesium sulfate), and is concentrated to give the crude methyl 9-alpha-acetoxy-11-alpha,15-alpha-bis-(tetrahydropyran-2-yloxy)-trans-13-16-p-biphenyl-prostenoate.

EXAMPLE 24

9-Alpha-Hydroxy-11-alpha, 15-alpha-bis-(tetrahydropyran-2-yloxy)-trans-13-16-p-biphenyl-ω-tetranorprostenoic acid A homogeneous solution of 0.350 g. (0.43 mmole) of the crude bis-THP ester prepared in Example 23, 1.3 ml. (1.30 mmoles) of a 1.0N aqueous sodium hydroxide solution, 1.3 ml. of methanol, and 1.3 ml. of tetrahydropyran is stirred under nitrogen overnight. The reaction is then quenched by the addition of 1.30 ml. (1.30 mmoles) of a 1.0N aqueous hydrochloric acid solution. The quenched solution is diluted with ethyl acetate. The organic layer is dried (anhydrous magnesium sulfate) and concentrated to afford the crude product. The crude product is purified by column chromatography to provide the 9-alpha-hydroxy-11-alpha,15-alpha-bis-(tetrahydropyran-2-yloxy)-trans-13-16-p-biphenyl-prostenoic acid.

The product of this example may be converted into 16-p-biphenyl-ω-tetranorprostaglandin $F_{1\text{-}alpha}$, $E_1$, $F_{1\text{-}beta}$, and $A_1$ by the procedures of Examples 8,9,10,11, and 14.

EXAMPLE 25

2-[5-alpha-Hydroxy-3-alpha(tetrahydropyran-2-yloxy)-2-beta-(3-alpha-{tetrahydropyran-2-yloxy}-5-phenyl-pent-1-yl)cyclopent-1-alpha-yl]acetic acid, gamma-lactone (24a)

A stirred heterogeneous solution of 1.555 g. (3.4 mmole) 2-[5-alpha-hydroxy-3-alpha(tetrahydropyran-2-yloxy)-2-beta-(3-alpha{tetrahydropyran-2-yloxy}-5-phenyl-trans-1-penten-1-yl)cyclopent-1-alpha-yl]acetic acid, gamma-lactone (7a) and 300 mg. 5% palladium on carbon in 35 ml. at absolute methanol is hydrogenated for 90 minutes. The reaction mixture is filtered through filter aid and concentrated (in vacuo) to yield 2-[5-alpha-hydroxy-3-alpha(tetrahydropyran-2-yloxy)-2-beta-(3-alpha-{tetrahydropyran-2-yloxy}-5-phenylpent-1-yl)cyclopentan-1-alpha-yl]acetic acid, gamma-lactone (24a).

The product of this example (24a) may be converted into the 13,14-dihydro-17-phenyl-ω-trisnorprostaglandin $E_2$, $F_{2\text{-}alpha}$, $F_{2\text{-}beta}$, and $A_2$ by the procedures of Examples 6-11 and 14.

EXAMPLE 26

2-[3-Alpha-p-Phenylbenzoyloxy-5-alpha-hydroxy-2-beta-(3alpha-hydroxy-3-beta-methyl-6-phenyl-trans-1-hexen-1-yl)cyclopent-1-alpha-yl]acetic acid, gamma-lactone (13a) and 2[3-alpha-p-Phenylbenzoyloxy-5-alpha-hydroxy-2-beta(3-beta-hydroxy-3-alpha-methyl-6-phenyl-trans-1-hexen-1-yl)cyclopent-1-alpha-yl]acetic acid gamma-lactone (14a).

To a solution of 2908 mg. (6.2 mmole) 2-[3-alpha-p-phenyl-benzoyloxy-5-alpha-hydroxy-2-beta-(3-oxo-6-phenyl-trans-1-hexen-1-yl)cyclopent-1-alpha-yl]acetic acid, gamma-lactone (3a) in 26 ml. anhydrous ether and 20 ml. of tetrahydrofuran (distilled from LAH) in a dry nitrogen atmosphere at −78° is added dropwise 6.8 ml. of (0.92$^M$) methyl lithium in ether (Alfa). After stirring at −78° for 15 minutes the reaction is quenched by the dropwise addition of glacial acetic acid until the pH of the reaction is approximately 7. The mixtures is then diluted with methylene chloride and the diluted organic solution is washed with water (IX) and with saturated brine (IX), is dried (anhydrous magnesium sulfate), and is concentrated to afford the epimeric alcohols.

The crude product is purified by column chromatography provides the 2-[3-alpha-p-phenylbenzoyloxy-5-alpha-hydroxy-2-beta-(3-alpha-hydroxy-3-beta-methyl-6-phenyl-trans-1-hexen-1-yl)cyclopent-1-alpha-yl]acetic acid, gamma-lactone (13a), and 2-[3-alpha-p-phenylbenzoyloxy-5-alpha-hydroxy-2-beta-(3-beta-hydroxy-3-alpha-methyl-6-phenyl-trans-1-hexen-yl)cyclopent-1-alpha-yl]acetic acid, gamma-lactone (14a).

This material (14a) may be converted to the 15-beta-methyl-18-phenyl-ω-tetranorprostaglandins of the A, E, and F series by the procedures outlined in Examples 4–14.

Other lower alkyl derivatives of the type (14a) may be prepared by substituting the approprite alkyl lithium derivative for methyl lithium in the above procedure. These derivatives are suitable for conversion to 15-lower alkyl-16-phenyl-ω-tetranorprostaglandins of the A, E, and F series through the sequences of Examples 4–14.

What is claimed is:

1. A compound of the structure:

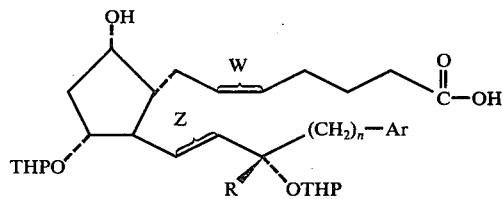

wherein

Ar is α- or β-naphthyl; phenyl; 3,4-dimethoxyphenyl; 3,4-methylenedioxyphenyl; 3,4,5-trimethoxyphenyl or monosubstituted phenyl wherein said substituent is halo, trifluoromethyl, phenyl, lower alkyl or lower alkoxy;

R is hydrogen or lower alkyl;

THP is 2-tetrahydropyranyl;

n is an integer from 1 to 5;

W is a single bond or a cis double bond;

and Z is a single bond or trans double bond; with the proviso that when n is one and Z is a single bond, W is a single bond.

2. A compound of the structure:

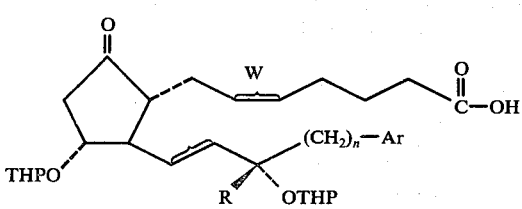

wherein

Ar is α- or β-naphthyl; phenyl; 3,4-dimethoxyphenyl; 3,4-methylenedioxyphenyl; 3,4,5-trimethoxyphenyl or monosubstituted phenyl wherein said substituent is halo, trifluoromethyl, phenyl, lower alkyl or lower alkoxy;

R is hydrogen or lower alkyl;

THP is 2-tetrahydropyranyl;

n is an integer from 1 to 5;

W is a single bond or a cis double bond;

and Z is a single bond or a trans double bond; with the proviso that when $n$ is one and Z is a single bond, W is a single bond.

3. The compound of claim 1 wherein Ar is a parabiphenyl; W is a cis double bond; Z is a trans double bond and $n$ is 1.

4. The compound of claim 2 wherein Ar is parabiphenyl; W is a cis double bond; Z is a trans double bond and $n$ is 1.

* * * * *